United States Patent
Susumu

(10) Patent No.: US 9,681,854 B2
(45) Date of Patent: Jun. 20, 2017

(54) ULTRASOUND SIGNAL PROCESSING DEVICE, ULTRASOUND SIGNAL PROCESSING METHOD, AND NON-TRANSITORY COMPUTER-READABLE RECORDING MEDIUM

(71) Applicant: KONICA MINOLTA, INC., Chiyoda-ku, Tokyo (JP)

(72) Inventor: Yasuaki Susumu, Osaka (JP)

(73) Assignee: KONICA MINOLTA, INC., Tokyo (JP)

( * ) Notice: Subject to any disclaimer, the term of this patent is extended or adjusted under 35 U.S.C. 154(b) by 170 days.

(21) Appl. No.: 14/331,823

(22) Filed: Jul. 15, 2014

(65) Prior Publication Data
US 2015/0025378 A1    Jan. 22, 2015

(30) Foreign Application Priority Data

Jul. 16, 2013  (JP) ................................ 2013-147249
Jul. 11, 2014  (JP) ................................ 2014-142955

(51) Int. Cl.
| | | |
|---|---|---|
| *A61B 8/08* | (2006.01) | |
| *G01S 7/52* | (2006.01) | |
| *G01S 15/89* | (2006.01) | |
| *A61B 5/00* | (2006.01) | |

(52) U.S. Cl.
CPC .......... *A61B 8/5207* (2013.01); *A61B 8/0891* (2013.01); *G01S 7/52047* (2013.01); *G01S 15/8915* (2013.01); *G01S 15/8961* (2013.01); *A61B 5/7228* (2013.01)

(58) Field of Classification Search
CPC ... A61B 5/7228; A61B 8/5207; A61B 8/0891; G01S 15/8915; G01S 15/8961; G01S 7/52047
See application file for complete search history.

(56) References Cited

U.S. PATENT DOCUMENTS

| | | |
|---|---|---|
| 5,984,869 A | 11/1999 | Chiao et al. |
| 6,113,545 A | 9/2000 | Chiao et al. |
| 6,350,240 B1 | 2/2002 | Song et al. |
| 7,354,400 B2 * | 4/2008 | Asafusa ............. G01S 7/52023 367/138 |
| 8,804,460 B1 * | 8/2014 | Price .................... G01S 3/8083 367/127 |
| 2007/0211786 A1 * | 9/2007 | Shattil .................. H04B 1/707 375/141 |

FOREIGN PATENT DOCUMENTS

| | | |
|---|---|---|
| JP | 3423935 B2 | 7/2003 |
| JP | 4472802 B2 | 6/2010 |

* cited by examiner

*Primary Examiner* — Vani Gupta
(74) *Attorney, Agent, or Firm* — Holtz, Holtz & Volek PC

(57) ABSTRACT

Preceding decoders each convolve a corresponding one of a plurality of transducer elements constituting a transducer element array of an ultrasound probe with an impulse response waveform, while varying a filter coefficient corresponding to time side lobes for each transmission event. A succeeding decoder stores, in a memory, a reception beam signal that is output from a reception beam former. When a new reception beam signal is output, the succeeding decoder performs delay-and-sum on the new reception beam signal and the reception beam signal, which has been output immediately before the new reception beam signal and is stored in the memory.

9 Claims, 17 Drawing Sheets

[Math. 11]
$$RxD_i(d) = \frac{\sqrt{d^2+(P \cdot i)^2}-d}{v}$$

Main lobe of reflected ultrasound wave corresponding to shallow part

Steep

Main lobe of reflected ultrasound wave corresponding to deep part

Flat

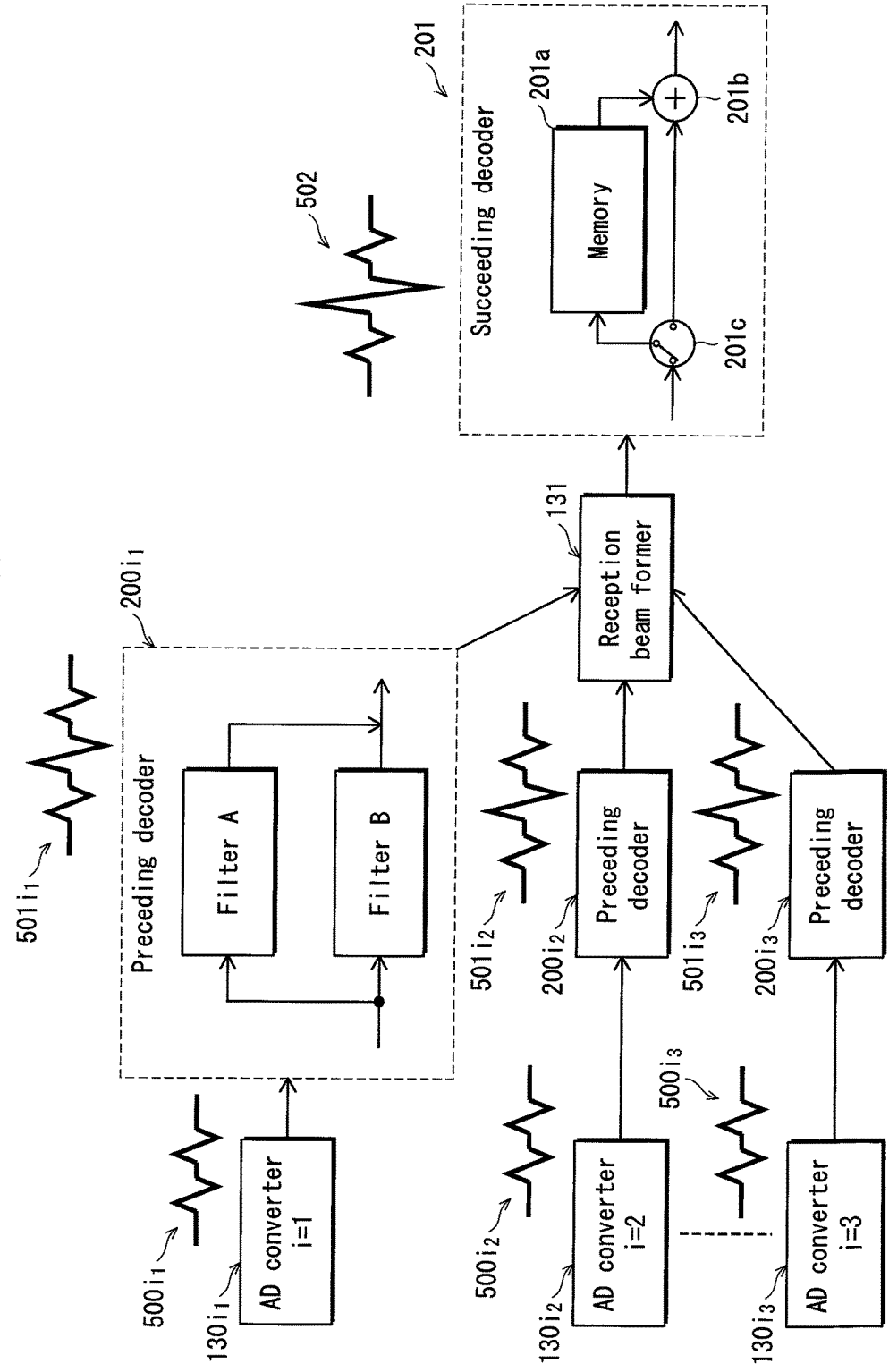

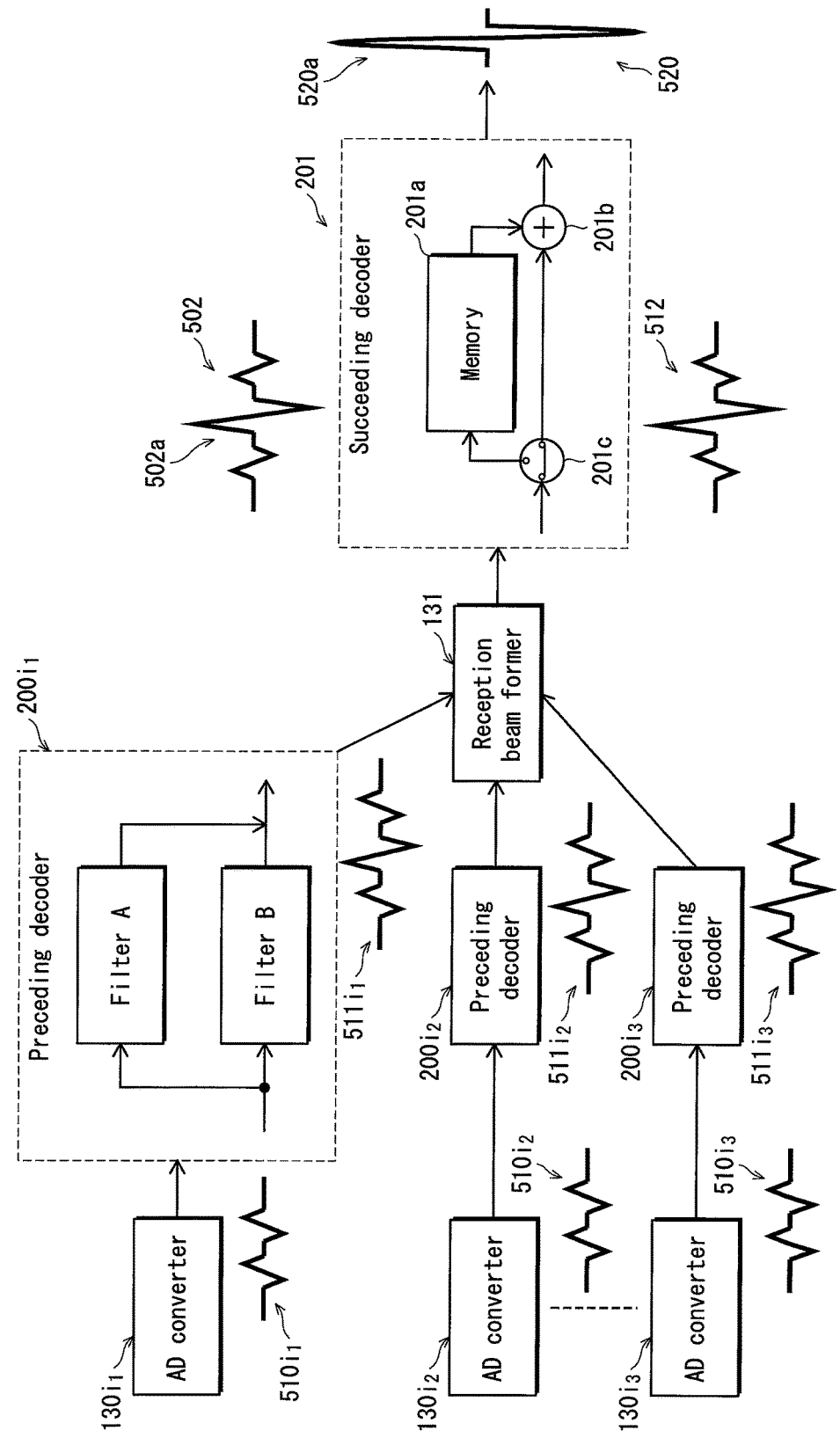

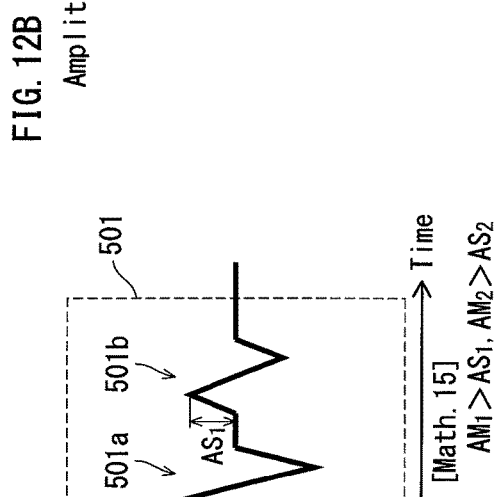
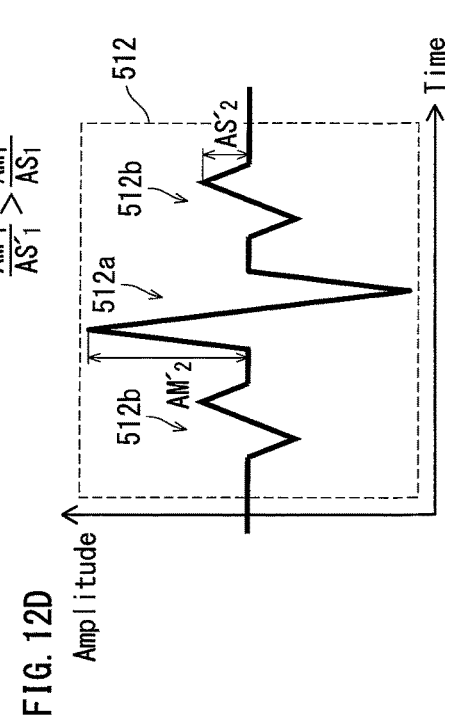
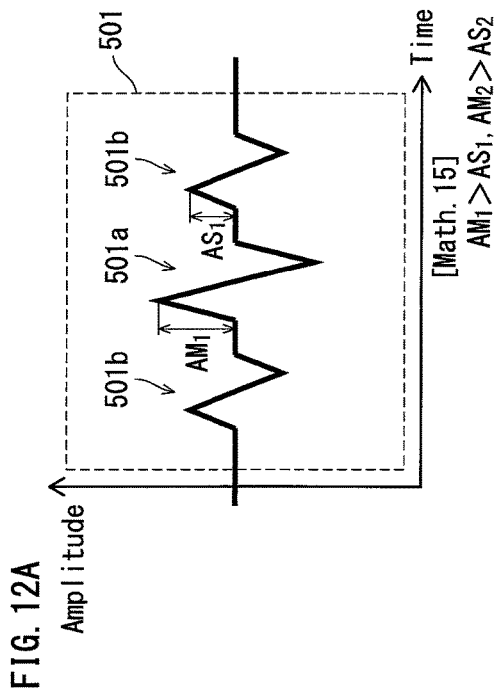
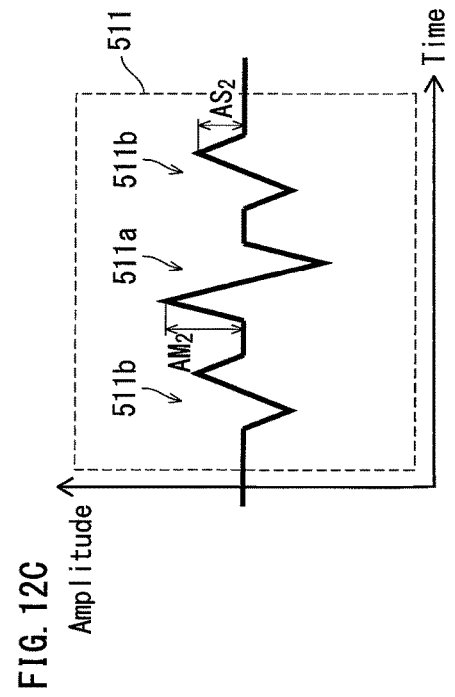

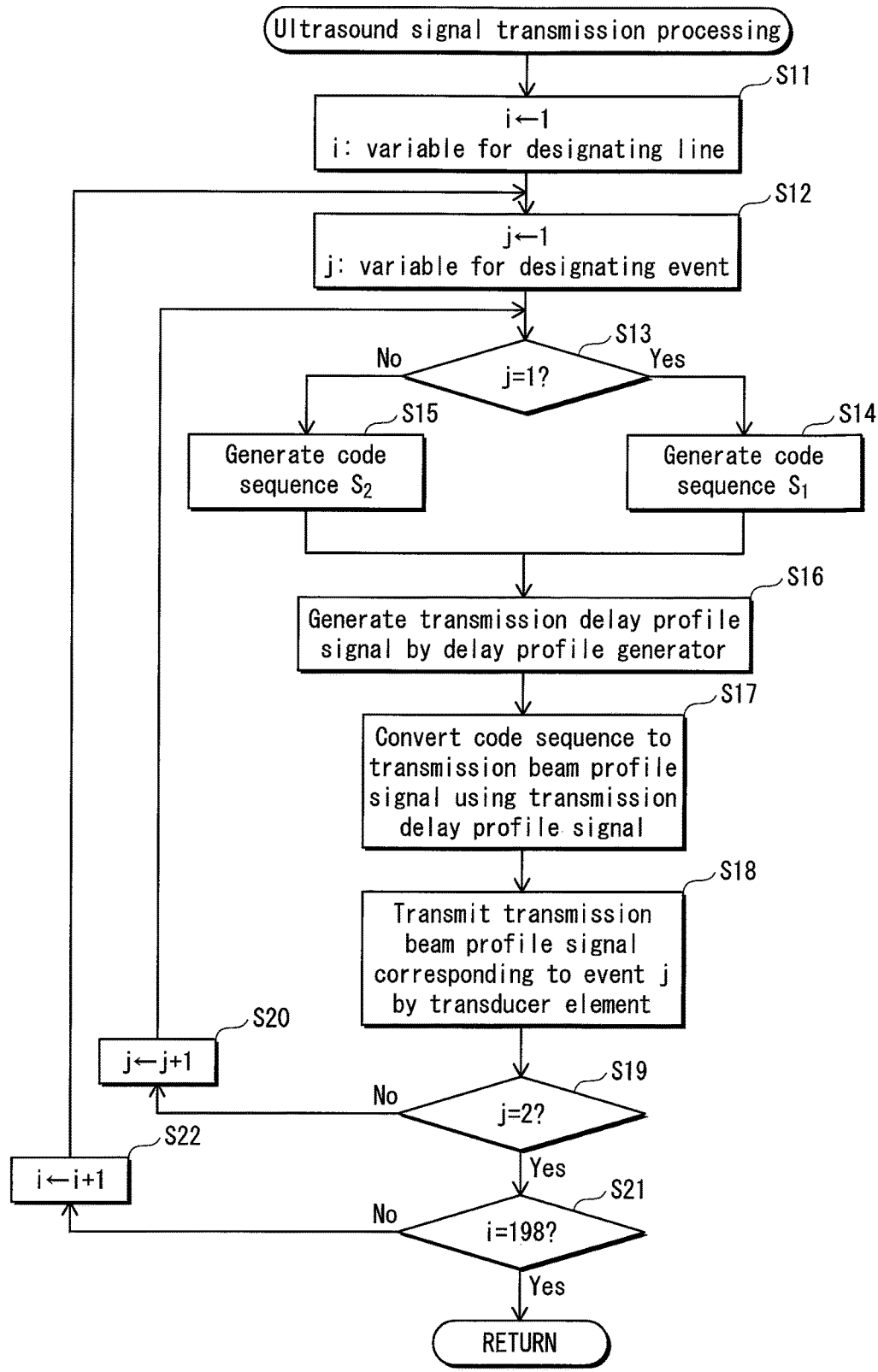

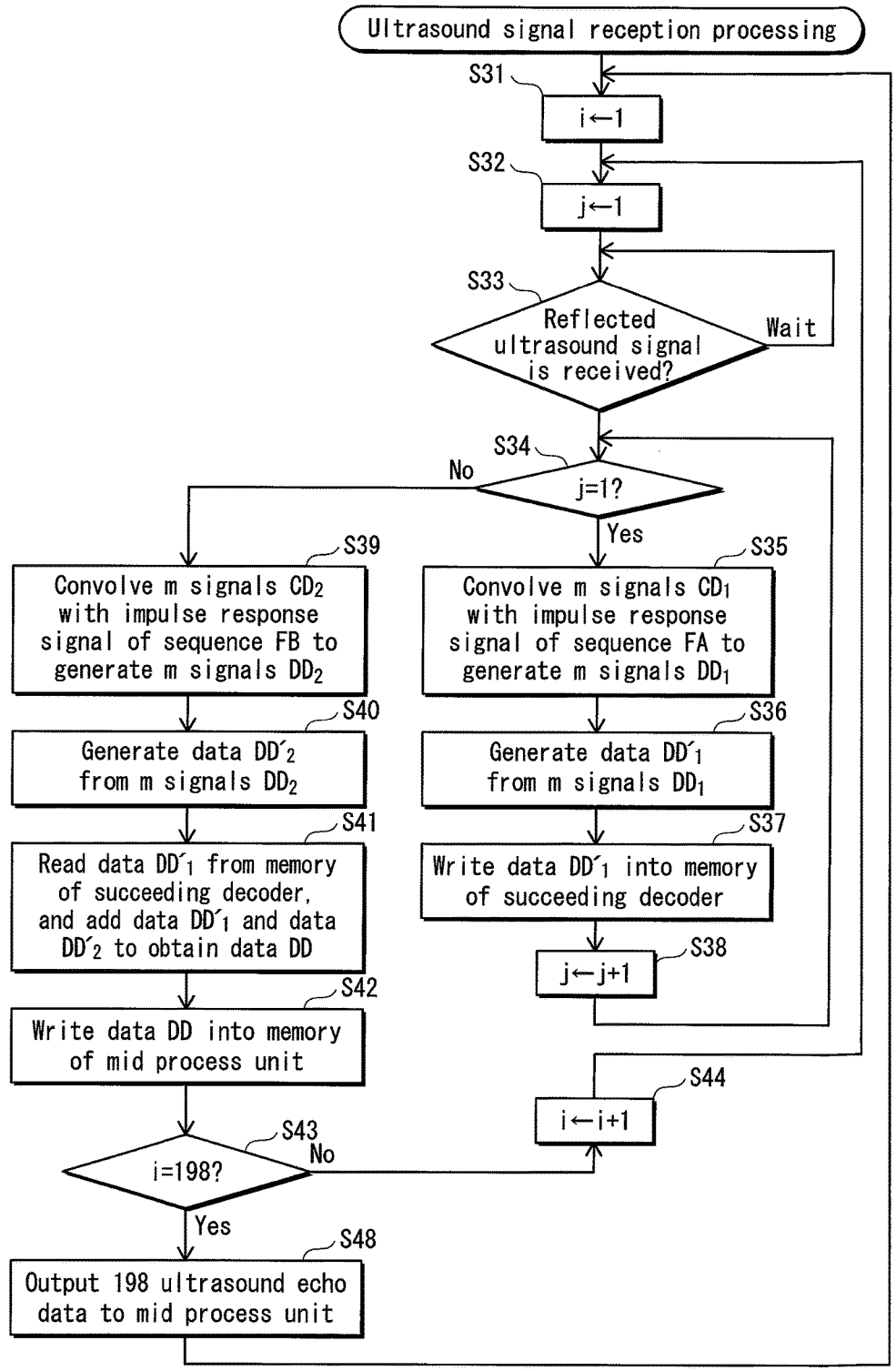

ULTRASOUND SIGNAL PROCESSING DEVICE, ULTRASOUND SIGNAL PROCESSING METHOD, AND NON-TRANSITORY COMPUTER-READABLE RECORDING MEDIUM

This application is based on an application No. 2013-147249 filed in Japan on Jul. 16, 2013 and an application No. 2014-142955 filed in Japan on Jul. 11, 2014, the contents of which are hereby incorporated by reference.

BACKGROUND OF THE INVENTION (1) Field of the Invention

The present invention belongs to a technical field of ultrasound signal transmission and reception processing, and particularly relates to decoding of code sequences coded by pulse compression.

(2) Description of the Related Art

According to ultrasound signal transmission and reception processing, transmission signals for transducer elements constituting an ultrasound probe are generated, and also delay-and-sum is performed on each of respective reception signals output from the transducer elements by a reception beam former so as to obtain a reception beam signal to generate an ultrasound echo signal. A pixel array corresponding to one line of an ultrasound image for ultrasound diagnosis is generated from the ultrasound echo signal. Since an S/N (sound/noise) ratio of ultrasound echo signals directly influences the quality of ultrasound images, pulse compression encoding as described above has been used in order to improve the S/N ratio. According to the pulse compression encoding, two or more code sequences differing in positive and negative code are transmitted in respective two or more transmission events. In ultrasound signal reception processing, a decoding unit performs filter processing and an event correlation operation on each of respective reception signals corresponding to the two or more code sequences.

SUMMARY OF THE INVENTION

By the way, as a decoding method for performing filter processing and event correlation operation, two decoding methods have been used including an RF decoding method for decoding signals input to a reception beam former (hereinafter, RF signals) and a DAS decoding method for decoding signals output from the reception beam former (hereinafter, DAS signals).

According to the RF decoding method, RF signals of a plurality of channels are input from a transducer element array to a reception beam former. In order to perform decoding in a preceding stage of the reception beam former, it is necessary to store the RF signals of the channels in a memory to perform an event correlation operation. Since the RF signals of the channels need to be stored in the memory, the size of a decoder is large.

According to the DAS decoding method compared with this, a decoder is provided in a succeeding stage of a reception beam former, and delay-and-sum is performed on RF signals in coded form. The code shape of the RF signals is lost due to the delay-and-sum on the RF signals in coded form, and there occurs a notable decrease in amplitude of a main lobe and a notable occurrence of time side lobes. This deteriorates the quality of decoded signals.

The present invention aims to provide an ultrasound signal processing device capable of suppressing increase in memory size while avoiding deterioration in quality of decoded signals. The above aim is achieved by an ultrasound signal processing device that outputs a plurality of code sequences to the transducer element array to cause the transducer element array to transmit ultrasound and receive reflected ultrasound, the code sequences each having a different arrangement of a plurality of code words, the ultrasound signal processing device comprising: preceding decoders that obtain convolution signals by convolving each of transducer element signals with an impulse response signal, the transducer element signals being output from the transducer element array upon reception of the reflected ultrasound, where M is an integer satisfying $2 \leq M \leq N$; a reception beam former that obtains a plurality of reception beam signals one-to-one corresponding to the code sequences by performing delay-and-sum on each of the convolution signals; and succeeding decoders that obtain ultrasound echo data by performing a correlation operation on each of the reception beam signals based on the code words included in the code sequence corresponding to the reception beam signal, where L is an integer satisfying $1 \leq L < M$.

BRIEF DESCRIPTION OF THE DRAWINGS

These and the other objects, advantages and features of the invention will become apparent from the following description thereof taken in conjunction with the accompanying drawings which illustrate a specific embodiment of the invention.

In the drawings:

FIG. 10 shows a process of signal storage by a memory 201a in a transmission event 1;

FIG. 11 shows a process of signal addition by an addition unit 201b in a transmission event 2;

FIG. 12A shows first incompletely-decoded data 501, FIG. 12B shows first incompletely-decoded ultrasound echo data 502, FIG. 12C shows second incompletely-decoded data 511, and FIG. 12D shows second incompletely-decoded ultrasound echo data 512;

FIG. 16 is a flow chart showing a procedure of ultrasound signal transmission processing; and FIG. 17 is a flow chart showing a procedure of ultrasound signal reception processing.

DESCRIPTION OF THE PREFERRED EMBODIMENTS

A trade-off relationship is established between the implementation load and the quality of decoded signals, in consideration of whether to output RF signals of a plurality of channels on which filter processing has been performed or to perform filter processing on DAS signals that are output from the reception beam former. In order to solve this trade-off relationship, the ultrasound signal processing device relating to the present embodiment includes preceding decoders and a succeeding decoder into which a conventional decoding unit is divided. The preceding decoders each perform filter processing in a preceding stage of a reception beam former, and the succeeding decoder performs an event correlation operation in a succeeding stage of the reception beam former. Specifically, the ultrasound signal processing device relating to the present invention is an ultrasound signal processing device that outputs a plurality of code sequences to the transducer element array to cause the transducer element array to transmit ultrasound and receive reflected ultrasound, the code sequences each having a different arrangement of a plurality of code words, the ultrasound signal processing device comprising: M preceding decoders that obtain N convolution signals by convolving each of N transducer element signals with an impulse response signal, the N transducer element signals being output from the transducer element array upon reception of the reflected ultrasound, where M is an integer satisfying $2 \leq M \leq N$; a reception beam former that obtains a plurality of reception beam signals one-to-one corresponding to the code sequences by performing delay-and-sum on each of the N convolution signals; and L succeeding decoders that obtain ultrasound echo data by performing a correlation operation on each of the reception beam signals based on the code words included in the code sequence corresponding to the reception beam signal, where L is an integer satisfying $1 \leq L < M$.

According to the ultrasound signal processing device having the above structure, filter processing is performed on each of the transducer element signals output from the transducer element array, and a correlation operation is performed on each of the reception beam signals output from the reception beam former. Accordingly, an influence of the time side lobes is not prominent even in the case where the event correlation operation is performed in the succeeding stage of the reception beam former. This reduces the storage region of the decoding unit while suppressing decrease in amplitude of the main lobe and occurrence of time side lobes.

Embodiment

Figure 1:
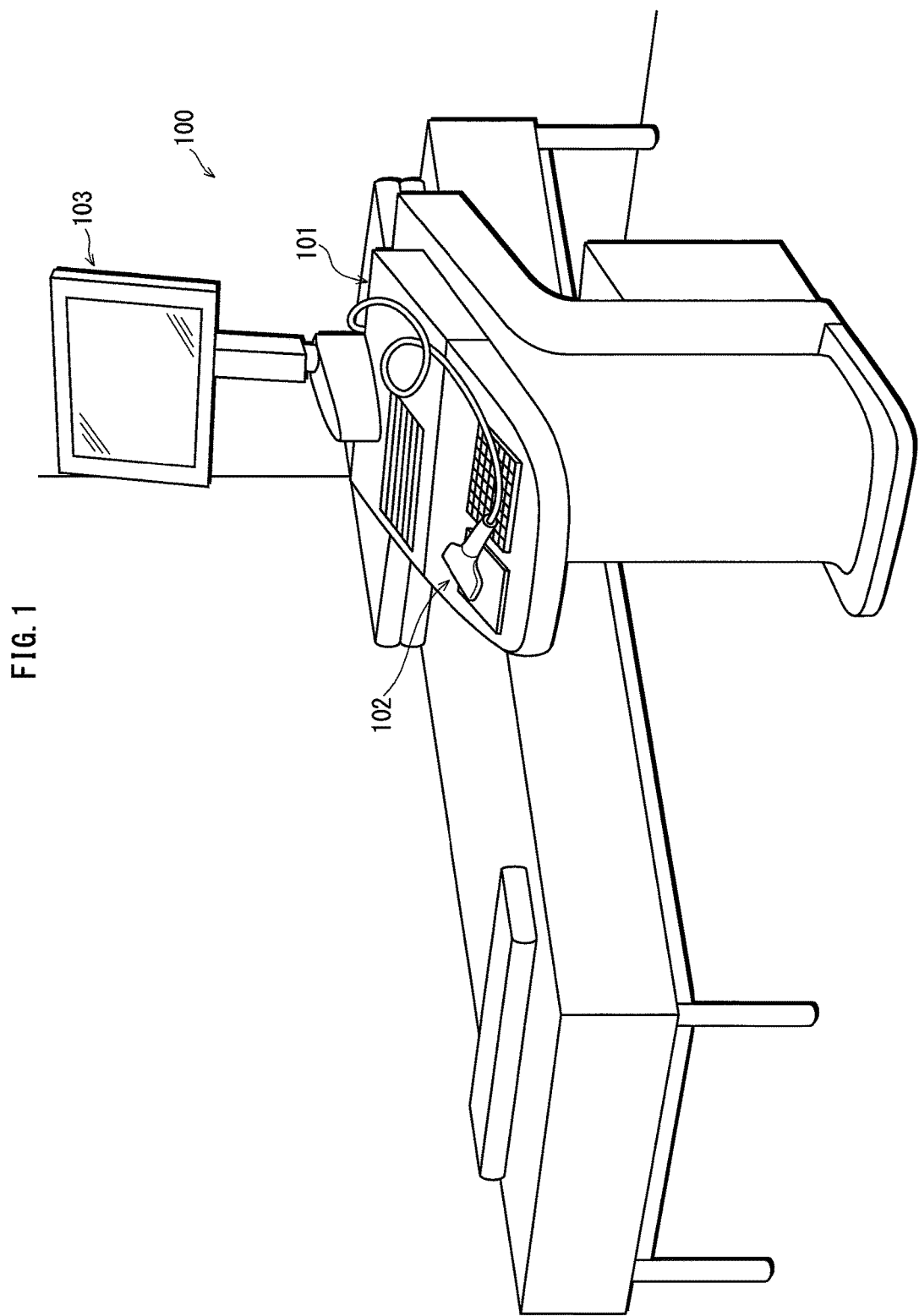
FIG. 1 shows an outer appearance structure of an ultrasound diagnostic system including an ultrasound signal processing device.

The following describes a schematic structure of an ultrasound signal processing device relating to the present embodiment. FIG. 1 shows an outer appearance structure of an ultrasound diagnostic system including an ultrasound signal processing device.

An ultrasound diagnostic system 100 includes an ultrasound signal processing device 101, an ultrasound probe 102, and a display unit 103.

The ultrasound signal processing device 101 performs transmission and reception of ultrasound signals and image formation of the received ultrasound signals in order to perform ultrasound diagnosis.

The ultrasound probe 102 includes therein a transducer element array, and transmits ultrasound and receives a reflected ultrasound signal that is reflected from a subject. The transducer element array is composed of a plurality of transducer elements 110. A reflected ultrasound wave which reflected off a reflection point spherically spreads to reach the transducer elements which are transmission originations. Accordingly, the reflected ultrasound wave reaches the transducer element the earliest which is positioned in a position vertically to the reflection point. The more distant from the vertical position the transducer element is positioned, the slower the reflected ultrasound wave reaches. Reflected ultrasound waves with various time delays reaches the transducer elements. Accordingly, the ultrasound signal processing device 101 performs ultrasound signal processing by performing delay-and-sum on the reflected ultrasound waves in consideration of time delays in the reflected ultrasound waves reaching the transducer elements.

Figure 2:
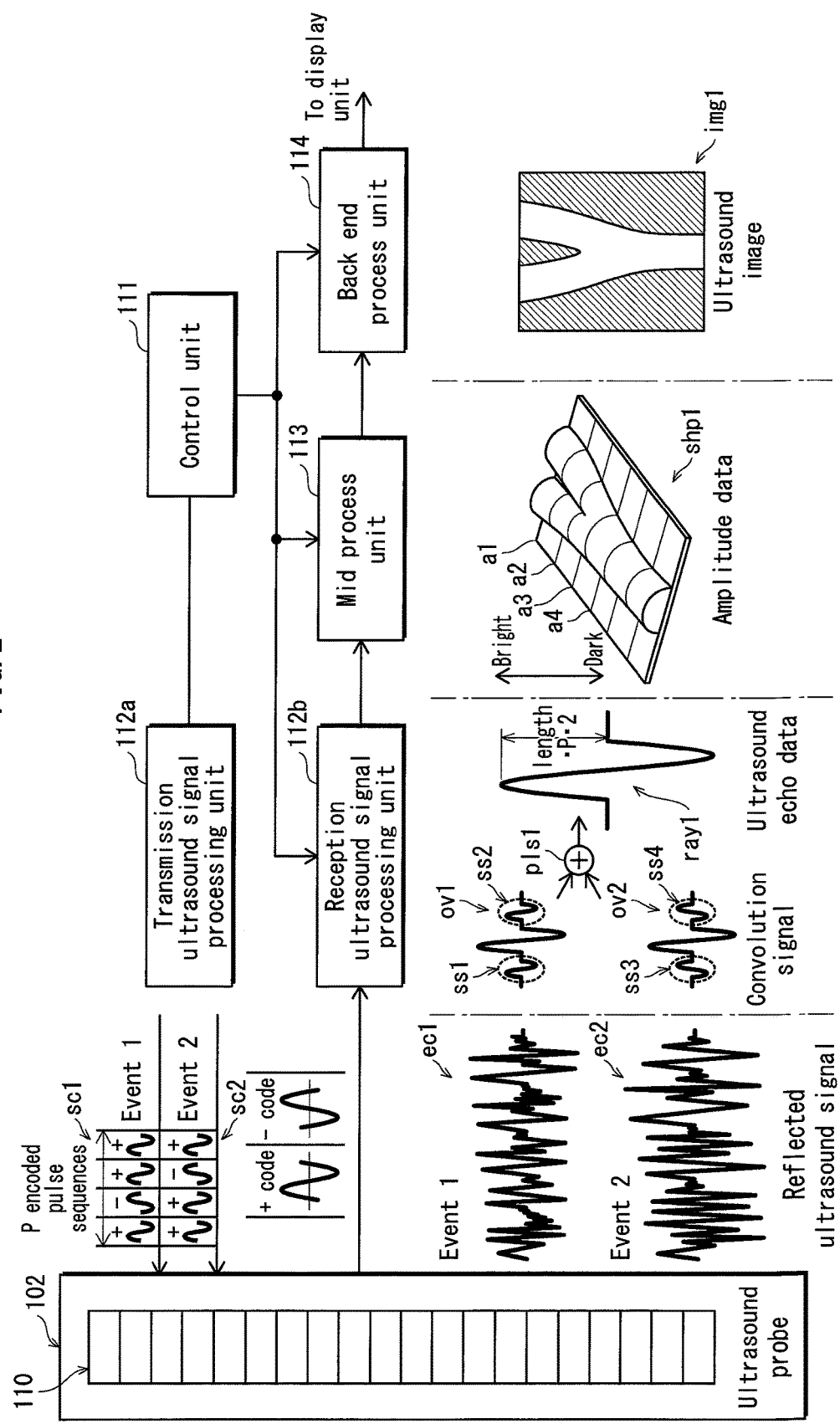
FIG. 2 is a diagram showing an internal structure of an ultrasound signal processing device 101 to which processing details are additionally written.

The display unit 103 is an LCD (Liquid Crystal Display) or the like, and displays B-mode images and so on that are generated from the reflected ultrasound signals. This completes the description of the ultrasound signal processing device 100. The following describes the internal structure of the ultrasound signal processing device 101. FIG. 2 is a diagram showing the internal structure of the ultrasound signal processing device 101. As shown in the figure, the ultrasound signal processing device 101 includes a control unit 111, a transmission ultrasound signal processing unit 112a, a reception ultrasound signal processing unit 112b, a mid process unit 113, and a back end process unit 114.

The control unit 111 generates a control signal, and outputs the control signal to the transmission ultrasound signal processing unit 112a, the mid process unit 113, and the back end process unit 114. The control signal, which is output from the control unit 111, includes beam profile information and code number information. The beam profile information defines beam profile that is formed from a transmission ultrasound signal, by designating a position of a beam focal point, designating a region in which transmitted ultrasound concentrates, and so on. The code number information defines the number of code sequences based on signal amplification.

The transmission ultrasound signal processing unit 112a generates a different code sequence in each of a plurality of transmission events, and outputs an ultrasound signal that is coded by the code sequence to the ultrasound probe 102 to causes the ultrasound probe 102 to perform ultrasound scanning. In FIG. 2, a reference sign sc1 represents a coded pulse sequence that is transmitted in the first time transmission event (transmission event 1) among two transmission events, and a reference sign sc2 represents a coded pulse sequence that is transmitted in the second time transmission event (transmission event 2) among the two transmission events. The coded pulse sequence sc1 represents a sequence of positive and negative codes +−++, and the coded pulse sequence sc2 represents a sequence of positive and negative codes ++−+. These two coded pulse sequences sc1 and sc2 are respectively transmitted in the transmission events 1 and 2. Here, the transmission event is an event that after a predetermined time period elapsed since ultrasound is transmitted into a subject, next ultrasound is transmitted into the subject.

The reception ultrasound signal processing unit 112b obtains reflected ultrasound through ultrasound scanning in each of the events. Then, the reception ultrasound signal processing unit 112b obtains ultrasound echo data by performing AD conversion, convolution of an impulse response signal, delay-and-sum, and event correlation operation on each of the reflected ultrasound signal which are output from the transducer elements 110 of the ultrasound probe 102. Note that the term data which is used in the expression of ultrasound echo data indicates a digitized signal waveform. Hereinafter in the present embodiment, the term data is used in this sense. In FIG. 2, reference signs ec1 and ec2 respectively represent a reflected ultrasound signal corresponding to the transmission event 1 and a reflected ultrasound signal corresponding to the transmission event 2. The reflected ultrasound signals ec1 and ec2 each have tailing due to the characteristics of the transducer elements. The tailing occurs as a result of an insufficient response of the transducer elements to an input waveform.

In the figure, a reference sign pls1 represents addition of the reflected ultrasound signals ec1 and ec2. A reference sign ov1 represents a convolution waveform that is obtained by convolving the reflected ultrasound signals ee1 with an impulse response waveform, and a reference sign ov2 represents a convolution waveform that is obtained by convolving the reflected ultrasound signals ec2 with an impulse response waveform. The convolution waveforms ov1 and ov2 are each composed of a single main lobe and time side lobes ss1, ss2, ss3, ss4 that are each precedent to or subsequent to the main lobe. The convolution waveforms ov1 and ov2 differ from each other in terms of that respective time side lobes are reversed in phase to each other. The tailing of the reflected ultrasound signal ec1 and the tailing of the reflected ultrasound signal ec2 are also reversed in phase to each other.

In the figure, a reference sign ray1 represents ultrasound echo data that is obtained by the addition pls1. Ultrasound echo data pieces are data pieces that constitute an ultrasound image after delay-and-sum and are continuous in the depth direction. The depth direction is a direction in which a transmission ultrasound signal travels from the surface of a body of a subject toward the inside of the body of the subject. The ultrasound echo data has no time side lobe as a result of cancellation. The main lobe of the ultrasound echo data has a pulse length (length·P·2) in accordance with the number of pulse waves (P pulse waves) constituting the code sequence.

The mid process unit 113 receives an input of the ultrasound echo data, generates amplitude data from the ultrasound echo data, and outputs the amplitude data to the back end process unit 114. Here, the amplitude data is data representing amplitude intensity of a reception ultrasound signal. In the figure, reference signs a1, a2, a3, a4, . . . represent amplitude data pieces that are obtained by processing a plurality of ultrasound echo data pieces. In the figure, a reference sign shp1 represents a three dimensional geometry of the subject that is reproduced by arranging the amplitude data pieces a1, a2, a3, a4, . . . in the vertical direction. The transverse direction of each of the amplitude data pieces corresponds to a line of a pixel array of an ultrasound image, and the wave height of the amplitude data piece indicates depth from the probe 102 to the subject.

Accordingly, the 3D geometry of the subject is reproduced by arranging these amplitude data pieces in the vertical direction. Note that the example in the figure shows a 3D geometry of a blood vessel that is diagnosed by the ultrasound diagnostic system 100.

The back end process unit 114 receives an input of the amplitude data pieces generated from the reflected ultrasound signals, generates image data from the amplitude data pieces, and outputs the image data to the display unit 103. Here, the image data is data that is obtained by converting the amplitude data pieces to a brightness value. In the figure, a reference sign img1 represents an ultrasound image that is obtained from the amplitude data pieces a1, a2, a3, a4, . . . .

Figure 3:
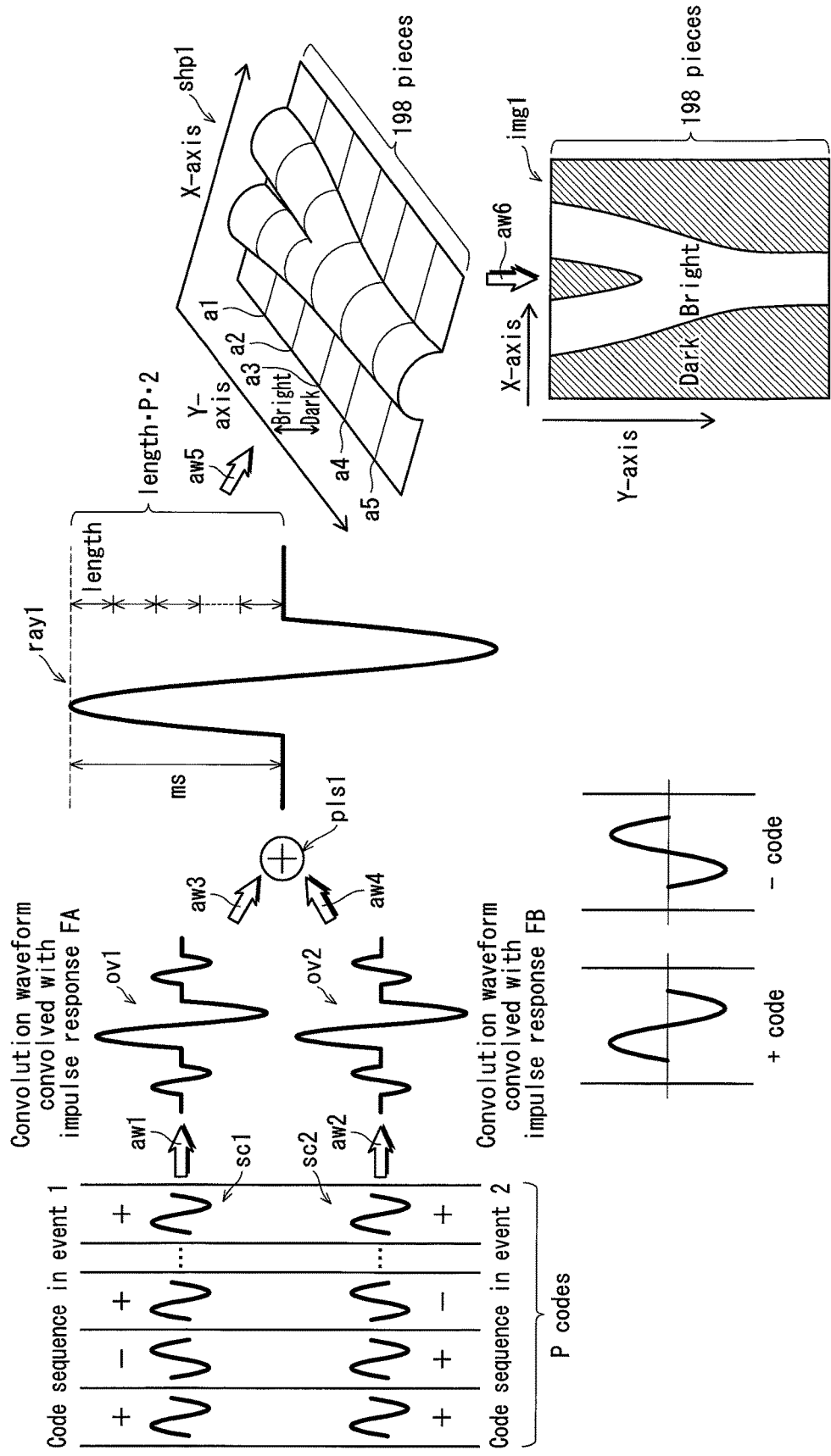
FIG. 3 shows coded pulse sequences sc1 and sc2, convolution waveforms ov1 and ov2, ultrasound echo data ray1, a three dimensional geometry shp1, and an ultrasound image img1 that are extracted from FIG. 2.

FIG. 3 shows the coded pulse sequences sc1 and sc2, the convolution waveforms ov1 and ov2, the ultrasound echo data ray1, the three dimensional geometry shp1, and the ultrasound image img1, which are extracted from FIG. 2. The figure schematically shows a process of performing ultrasound scanning on a subject by the ultrasound probe 102, receiving reflected ultrasound, and generating an image based on reflected ultrasound signals. As shown in the figure, the ultrasound signal processing device 101 obtains a reflected ultrasound signal by performing ultrasound scanning of the coded pulse sequences sc1 and sc2 on the subject, and convolves the reflected ultrasound signal with an impulse response signal, and thereby obtains the convolution waveforms ov1 and ov2 (arrows aw1 and aw2). Then, the ultrasound signal processing device 101 obtain the ultrasound echo data ray 1 by adding the convolution waveforms ov1 and ov2 (arrows aw3 and aw4), obtains amplitude data pieces a1, a2, a3, a4, . . . from the ultrasound echo data pieces (arrow aw5), and finally obtains the ultrasound image img1 (aw6).

Here, a brief description is given on the concept of pulse compression. By setting the pulse wave number of the transmission ultrasound signal to P, the ultrasound echo data ray1 has a main lobe whose amplitude is P times longer than a normal amplitude (length·P·2 in the figure).

The characteristics of the Golay code lie in that a reflected ultrasound wave received by the transducer element is convolved with a filter, and respective time side lobes corresponding to two transmission and reception (transmission events 1 and 2) are reversed in phase to each other.

Figure 4:
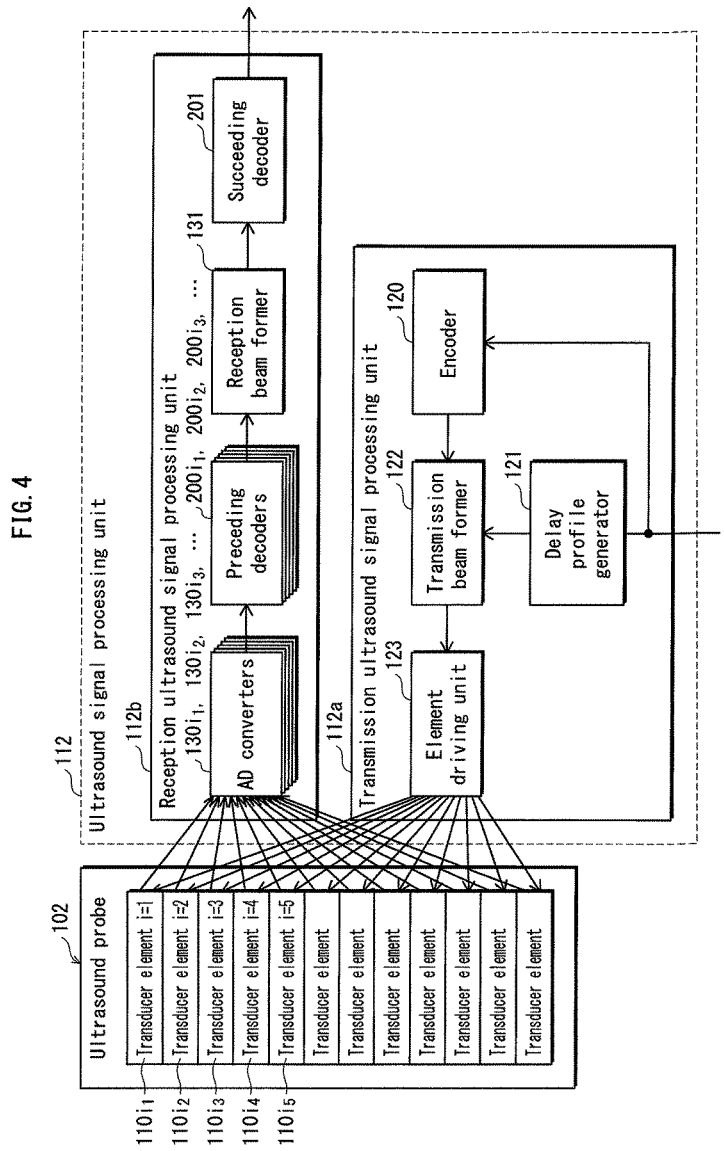
FIG. 4 shows an internal structure of an ultrasound signal processing unit 112.

The following describes the internal structure of the ultrasound signal processing unit 112. FIG. 4 shows the internal structure of the ultrasound signal processing unit 112. As shown in the figure, the ultrasound signal processing unit 112 includes a transmission ultrasound signal processing unit 112a and a reception ultrasound signal processing unit 112b.

Figure 5:
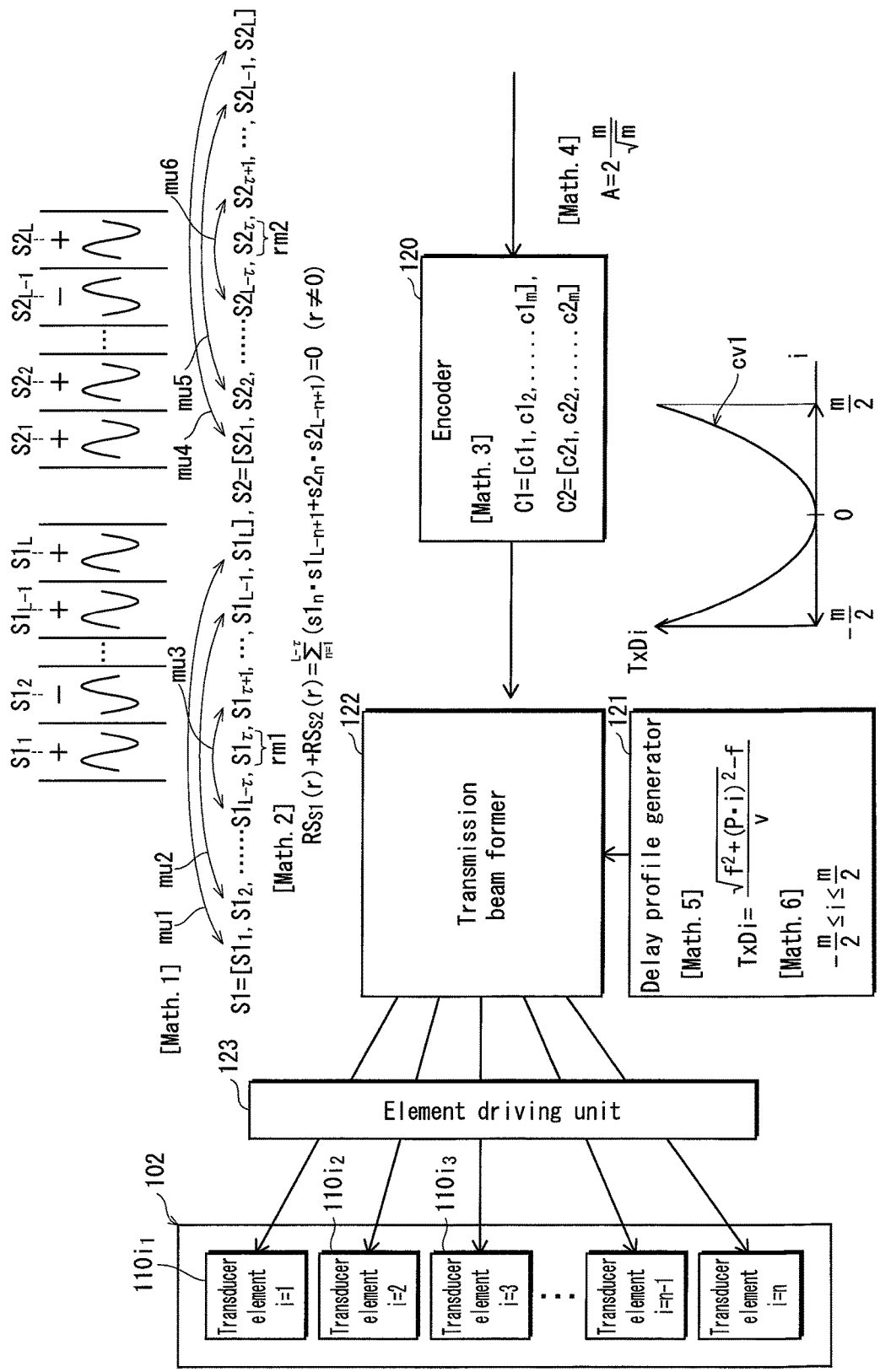
FIG. 5 is a diagram showing an encoder 120, a delay profile generator 121, a transmission beam former 122, and an element driving unit 123 that are extracted, to which processing details are additionally written.

The following describes constituent elements of the transmission ultrasound signal processing unit 112a. FIG. 5 is a diagram showing an encoder 120, a delay profile generator 121, a transmission beam former 122, and an element driving unit 123 that are extracted from the transmission ultrasound signal processing unit 112a, to which processing details are additionally written.

The encoder 120 generates a code sequence to be used for encoding a pulse sequence that is transmitted during two events of the transmission events 1 and 2. The Golay code is used here as a representative pulse compression method. The Golay code is a code sequence in which the sum of an aperiodic autocorrelation function of two code sequences is zero except the zero shift point. Code sequences S1 and S2 in Math. 1 shown below each represent a Golay code having the same length L and binary phases (positive (+) code and negative (−) code). FIG. 5 shows, in the upper right side, respective pulse waveform sequences of the code sequences S1 and S2. The positive codes of the code sequences S1 and S2 are each represented by a sine wave, and the negative codes of the code sequences S1 and S2 are each represented by a reversed-phase sine wave.

$$S1=[s1_1, s1_2, \ldots s1_L], S2=[s2_1, s2_2, \ldots, s2_L] \quad [\text{Math. 1}]$$

The positive code and the negative code, which are represented in waveform, differ from each other at least in phase. Generally, the positive code and the negative code differ from each other in phase by approximately 180 degrees. Hereinafter, the binary phase Golay code is used for the following description. In the figure, the code sequence S1 is a code sequence to be used for transmission in the transmission event 1, and the code sequence S2 is a code sequence to be used for transmission in the transmission event 2. The code sequences S1 and S2 satisfy conditions in Math. 2 and Math. 3 shown below.

$$RS_{S1}(\tau) + RS_{S2}(\tau) = \sum_{n=1}^{L-\tau} (s1_n s1_{L-n+1} + s2_n s2_{L-n+1}) = 0 \quad [\text{Math. 2}]$$

$$(\tau \neq 0)$$

In Math. 2, RS represents an autocorrelation function, and τ represents time shift. Ultrasound signal processing by the Golay code in ultrasound diagnosis generally requires respective two transmission events corresponding to the code sequences S1 and S2. In Math. 2, the term $S1_n S1_{L-n+1}$ represents the product of the n-th code from the beginning of the code sequence S1 and a code that is n−1 codes behind the end code of the code sequence S1, and the term $S2_n S2_{L-n+1}$ represents the product of the n-th code from the beginning of the code sequence S2 and a code that is n−1 codes behind the end code of the code sequence S2. Also, Σ operation represents summation of $S1_n S1_{L-n+1}$ and $S2_n S2_{L-n+1}$ within a range of n=1, t=1 to t=L−τ.

Math. 2 is also shown in the figure. In the figure, reference signs mu1, mu2, mu3, mu4, mu5, and mu6 each indicate a pair of code words that are multiplication targets in Math. 2, and reference signs rm1 and rm2 each represent a code word that is not a multiplication target. According to Math. 2, the code words that are multiplication targets, which are indicated by the pairs mu1, mu2, mu3, mu4, mu5, and mu6, are multiplied by each other, and results of the multiplications are added to each other, and finally the summation reaches zero. Then, the code words indicated by the reference signs rm1 and rm2, namely, the code words $S1_\tau$ and $S2_\tau$ are left. The code words $S1_\tau$ and $S2_\tau$ each correspond to a zero shift point. The ultrasound signal processing device 101 cancels the time side lobes by transmitting codes including codes that cancel each other.

When a Golay code corresponding to the transmission event 1 is represented as c1, a Golay code corresponding to the transmission event 2 is represented as c2, a first code sequence signal C1 and a second code sequence signal C2 are expressed by Math. 3 shown below.

$$C1=[c1_1, c1_2, \ldots c1_m], C2=[c2_1, c2_2, \ldots c2_m] \quad [\text{Math. 3}]$$

In Math. 3, m represents the number of codes that are generated in one transmission event.

An S/N ratio of ultrasound echo data is expressed by an increase value A in Math. 4 shown below. The increase value A, which expresses the S/N ratio, is a quotient of m by a square root of m.

$$A = 2 \frac{m}{\sqrt{m}} \quad [\text{Math. 4}]$$

Hereinafter, a signal that is generated in the transmission event 1 is has a name starting with the term first, and a signal that is generated in the transmission event 2 has a name starting with the term second for distinguishing from each other. Specifically, respective signals that are output from the encoder 120 in the transmission events 1 and 2 are referred to as a first code sequence signal and a second code sequence signal, respectively. The first code sequence signal and the second code sequence signal are each an information piece for encoding a transmission ultrasound signal beforehand, and are each constituted from a Golay code. This completes the description of the encoder 120.

The delay profile generator 121 receives an input of a control signal output from the control unit 111, generates a transmission delay profile signal from the control signal, and outputs the transmission delay profile signal to the transmission beam former 122. Here, the transmission delay profile signal is transmission delay profile information indicating a timing of driving each of the transducer elements 110 of the ultrasound probe 102 corresponding to an ultrasound beam formed from a transmission ultrasound signal.

The transmission beam former 122 gives a delay time corresponding to the transducer element 110, and outputs a coded pulse sequence to the transducer element 110. Giving of a delay time corresponding to the transducer element 110 is expressed by Math. 5 shown below.

$$TxD_i = \frac{\sqrt{f^2 + (p \cdot i)^2} - f}{v} \quad [\text{Math. 5}]$$

In Math. 5, $TxD_i$ represents a transmission delay profile signal having a single focal point, f represents a focal point of, a transmission ultrasound signal, p represents an interval between transducer elements, v represents sound velocity, and i represents an element number of the transducer element 110. When the transducer element 110 at the center in the transducer element array has an element number i=0, i and m satisfy a condition in Math. 6 shown below.

$$-\frac{m}{2} \leq i \leq \frac{m}{2} \quad [\text{Math. 6}]$$

In Math. 6, m represents the number of transducer elements 110 of the transducer element array.

In Math. 6, i represents change within a range of −m/2 to m/2, and has a value of zero in the transducer element 110 at the center in the transducer element array, and accordingly the term (p·i) corresponding to the transducer element 110 at the center in the transducer element array has a value of zero. As a result, since the numerator in Math. 5 is zero, the transmission delay profile signal $TxD_i$ corresponding to the transducer element 110 at the center in the transducer element array has a value of zero. On the other hand, the term (p·i) has a value changing in accordance with the distance from the transducer element 110 at the center in the transducer element array. FIG. 5 shows, in the lower right side, a graph of a change curve cv1 representing difference in drive timing of the transducer elements 110. The change curve cv1 has a transmission reference point i=0. In the change curve cv1, the horizontal axis represents element position of the transducer elements 110, and the vertical axis represents element drive timing of the transducer elements 110. The closer to the edges of the transducer element array the transducer element 110 is located, the earlier timing than the transmission reference point the drive timing of the transmission delay profile signal $TxD_i$ has.

Respective signals output from the transmission beam former 122 in the transmission events 1 and 2 are hereinafter referred to, as a first transmission beam profile signal and a second transmission beam profile signal, respectively. The first transmission beam profile signal and the second transmission beam profile signal are each obtained by changing a drive timing of a transmission delay profile corresponding to a focal point formed from a transmission ultrasound signal. The first transmission beam profile signal and the second transmission beam profile signal each indicate a drive timing of driving the transducer element 110 and a code shape of a code to be generated from ultrasound.

The drive timing is determined by the transmission delay profile signal which is generated by the delay profile generator 121, and indicates relative temporal difference in driving of the transducer element 110.

The respective code shapes of the first transmission beam profile signal and the second transmission beam profile signal are respectively determined by the first code sequence signal and the second code sequence signal which are generated by the encoder 120, and indicate a voltage pattern for exciting the transducer element 110.

The element drive unit 123 receives an input of the first transmission beam profile signal and the second transmission beam profile signal, generates respective drive signals from the first transmission beam profile signal and the second transmission beam profile signal, and outputs each of the drive signals to the transducer element 110.

The ultrasound probe 102 is composed of the transducer elements 110 which are the same constitute elements.

Figure 6:
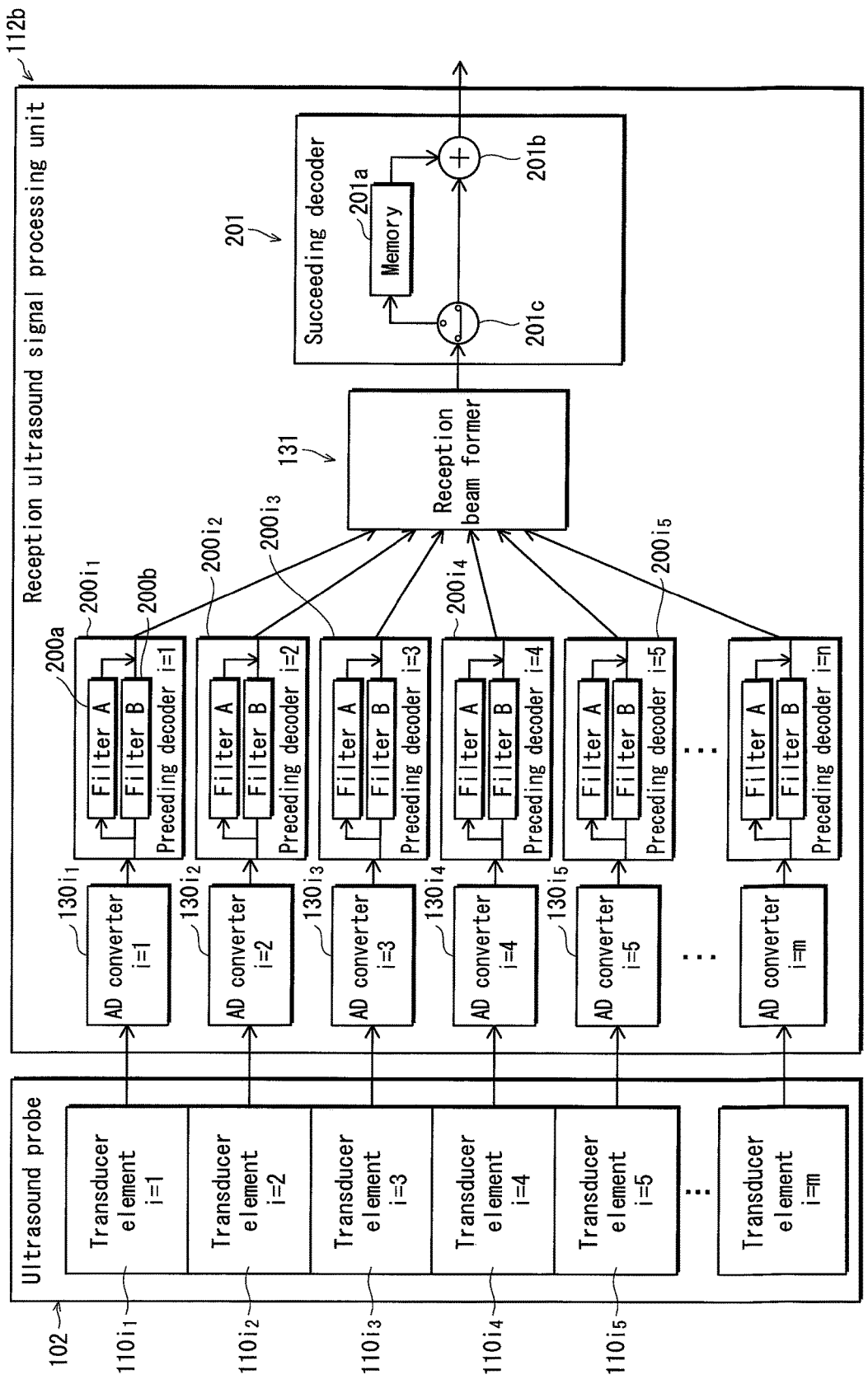
FIG. 6 shows an internal structure of a reception ultrasound signal processing unit 112b.

This completes the description of the transmission ultrasound signal processing unit 112a. The following describes in detail the reception ultrasound signal processing unit 112b. FIG. 6 shows the internal structure of the reception ultrasound signal processing unit 112b. As shown in the figure, the reception ultrasound signal processing unit 112b includes AD converters $130i_1$, $130i_2$, $130i_3$, . . . , which are equal in number to the transducer elements 110 included in the ultrasound probe 102, preceding decoders $200i_1$, $200i_2$, $200i_3$, . . . , which are equal in number to the transducer elements 110 included in the ultrasound probe 102, a single reception beam former 131, and a single succeeding decoder 201.

The AD converters $130i_1$, $130i_2$, $130i_3$, . . . are m AD converters 130 that are the same constituent elements. The AD converters $130i_1$, $130i_2$, $130i_3$, . . . are each indicated by a variable i ranging from one to m. Alphanumeric characters $i_1$, $i_2$, $i_3$, . . . following the reference sign 130 are simplified forms of i=1, i=2, i=3, . . . . The AD converters 130 each convert a reflected ultrasound signal, which is output from the transducer element 110, from an analog signal to a digital signal, and output the digital signal. Respective data pieces which are output from the AD converters 130 to the preceding decoder 200 in the transmission event 1 and 2 are hereinafter referred to as first coded ultrasound data and second coded ultrasound data, respectively. The first coded ultrasound data and the second coded ultrasound data are each ultrasound data that is obtained by digitizing a reflected ultrasound signal, and has code information. The first coded ultrasound data and the second coded ultrasound data each include real image information and artifact information. The real image information and the artifact information are separated by a filter included in each of the preceding decoders 200, and an event correlation operation is performed by the succeeding decoder 201. As a result, artifact components are removed.

The preceding decoders $200i_1$, $200i_2$, $200i_3$, . . . are m preceding decoders 200 that are the same constituent elements. The preceding decoders $200i_1$, $200i_2$, $200i_3$, . . . basically have the common internal structure, and are each indicated by a variable i ranging from one to m. Alphanumeric characters $i_1$, $i_2$, $i_3$, . . . following the reference sign 200 are simplified forms of i=1, i=2, i=3, . . . . The preceding decoders 200 each include a filter A200a and a filter B200b. The filter A200a convolves a reflected ultrasound signal $CD_1$ corresponding to the transmission event 1 with an impulse response signal of a filter coefficient sequence FA. The filter B200b convolves a reflected ultrasound signal $CD_2$ corresponding to the transmission event 2 with an impulse response signal of a filter coefficient sequence FB. Respective data pieces that are output from the preceding decoder 200 to the reception beam former 131 in the transmission events 1 and 2 are hereinafter referred to as first incompletely-decoded data and second incompletely-decoded data, respectively. The first incompletely-decoded data and the second incompletely-decoded data are each decoded ultrasound data that is generated by performing filter processing on coded ultrasound data, and has time side lobes.

The reception beam former 131 performs delay-and-sum by giving a delay time corresponding to an element position to a transducer element signal with which an impulse response waveform is convolved by the preceding decoder 200, and thereby obtains respective reception beam data pieces corresponding to the transmission events 1 and 2. Respective reception beam data pieces which are output from the reception beam former 131 to the succeeding decoder 201 in the transmission events 1 and 2 are hereinafter referred to as first incompletely-decoded ultrasound echo data and second incompletely-decoded ultrasound echo data, respectively. The first incompletely-decoded ultrasound echo data and the second incompletely-decoded ultrasound echo data are each data that is generated by delay-and-sum and has continuity in the depth direction. Difference among the first incompletely-decoded ultrasound echo data, the second incompletely-decoded ultrasound echo data, and the ultrasound echo data lies in that while the ultrasound echo data has no time side lobe, the first incompletely-decoded ultrasound echo data and the second incompletely-decoded ultrasound echo data each have time side lobes.

Note that a reflected ultrasound wave which reflected off a reflection point spherically spreads to reach the transducer elements. Accordingly, the reflected ultrasound wave reaches the transducer element which is positioned in a position vertically to the reflection point. The more distant from the vertical position the transducer element is positioned, the slower the reflected ultrasound wave reaches. For this reason, the reception beam former 131 adds the respective reflected ultrasound waves that are received by the transducer elements in consideration of this time delay, and thereby increases the S/N ratio of the reflected ultrasound waves.

The succeeding decoder 201 converts reception beam data corresponding to each event to ultrasound echo data.

Figures 7A, 7B:
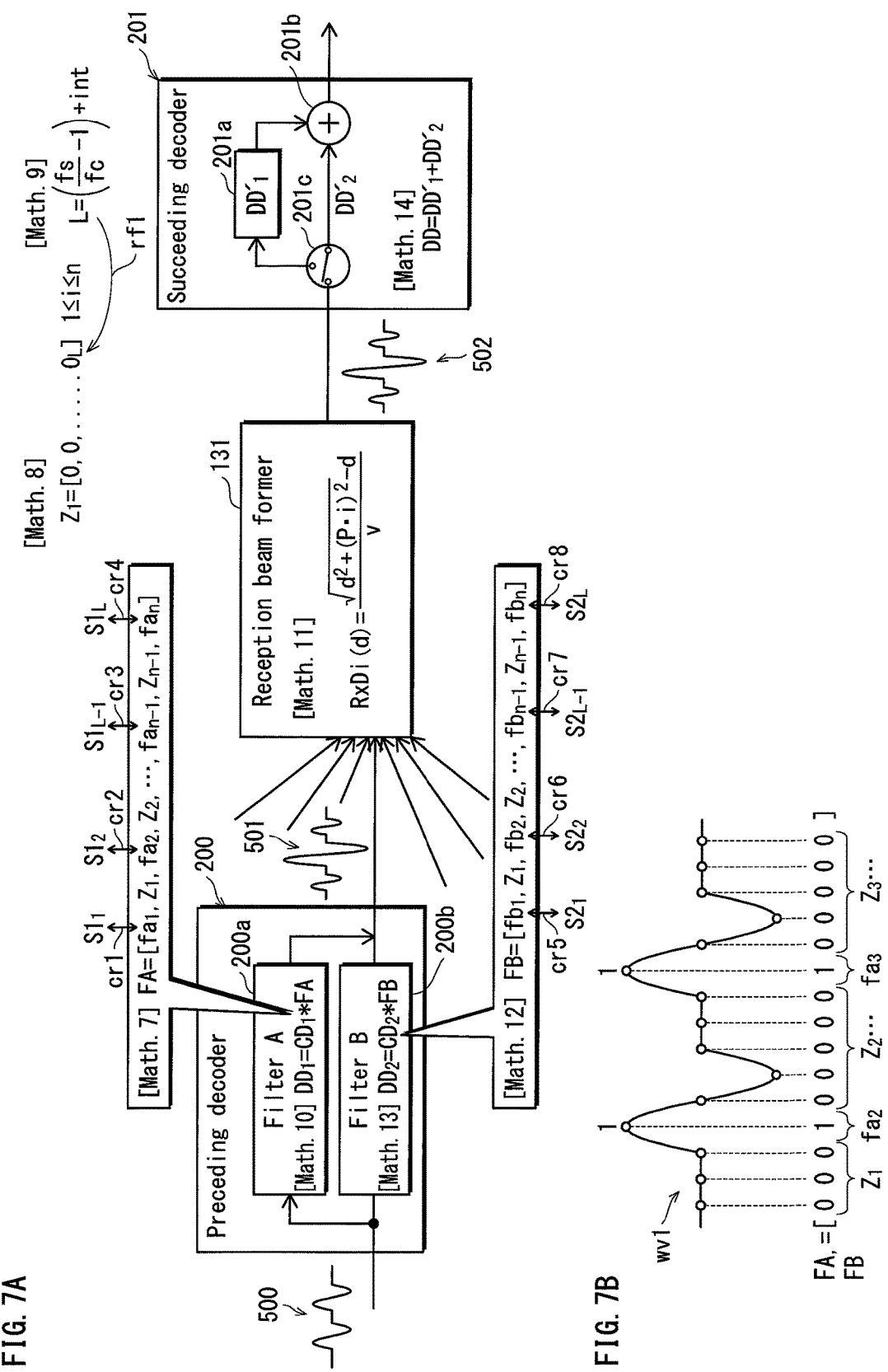
FIG. 7A shows an internal structure of a preceding decoder 200, a reception beam former 131, and a succeeding decoder 201.
FIG. 7B shows a relationship between a waveform of an RF signal and a filter coefficient sequence FA.

The following describes the internal structure of the preceding decoder 200, the reception beam former 131, and the succeeding decoder 201, with reference to FIG. 7A. FIG. 7A is a diagram showing the preceding decoder 200, the reception beam former 131, and the succeeding decoder 201 which are extracted from FIG. 6, to which processing details are additionally written.

The reception beam former 131 obtains reception beam data by giving a delay time to a transducer element signal output from the transducer element 110 having the element number i and performing delay-and-sum.

The succeeding decoder 201 includes a memory 201a that stores therein reception beam data that is output from the reception beam former 131, an addition unit 201b that performs addition of the reception beam data stored in the memory 201a and reception beam data corresponding to the transmit event 2, and a switch 201c that switches whether to skip storage by the memory 201a. Ultrasound echo data is obtained by the addition unit 201b performing addition.

Filter processing (filter A) corresponding to the transmission event 1 is expressed by Math. 7 shown below.

$$FA=[fa_1,Z_1,fa_2,Z_2, \ldots ,fa_{n-1},Z_{n-1},fa_n] \quad \text{[Math. 7]}$$

In Math. 7, $fa_i$ represents a filter coefficient. Math. 7 is also shown in FIG. 7. In the figure, reference signs cr1, cr2, cr3, and cr4 respectively represent a relationship between $fa_1$ in Math. 7 and $S1_1$ in Math. 1, a relationship between $fa_2$ in Math. 7 and $S1_2$ in Math. 1, a relationship between $fa_{n-1}$ in Math. 7 and $S1_{L-1}$ in Math. 1, and a relationship between $fa_n$ in Math. 7 and $S1_L$ in Math. 1. A main lobe of ultrasound echo data is generated from the entire filter coefficients in Math. 7. Here, a zero interval is represented as $Z_n$ (n=1, 2, 3, . . . ), and is expressed by Math. 8 shown below.

$$Z_i=[0,0, \ldots ,0_L] \quad 1 \le i \le n \quad \text{[Math. 8]}$$

In Math. 8, L represents length of the zero interval. A reference sign rf1 in the figure represents that the length L is defined by Math. 9 shown below.

$$L = \left(\frac{fs}{fc} - 1\right) + \text{int} \quad \text{[Math. 9]}$$

In Math. 9, fs represents a sampling frequency, fc represents a center frequency of a transmission ultrasound signal, and int represents an arbitrary number of insertion of zero.

FIG. 7B shows a relationship between a signal waveform of an RF signal and the filter coefficient sequence FA. In the figure, a reference sign wv1 represents a signal waveform in which intervals are given between main lobes in accordance with the zero intervals $z_1$, $z_2$, and $z_3$, . . . in the filter coefficient sequences FA and FB. Respective vertices of the main lobes correspond to the filter coefficients $fa_2$ and $fa_3$, respectively. The zero intervals $z_1$, $z_2$, and $z_3$, . . . each define an interval between the vertices of the main lobes. In other words, definition of an arbitrary number of zero by the zero intervals $z_1$, $z_2$, and $z_3$, . . . results in definition of an interval between a vertex of a certain main lobe and a vertex of a main lobe subsequent to the certain main lobe. The zero interval $z_1$ in front of the vertex $fa_2$ is a code sequence of 000, and accordingly an interval in front of the vertex $fa_2$ is defined. Also, the zero interval $z_2$ is a code sequence of 00000, and accordingly an interval between the vertices $fa_2$ and $fa_3$ of the main lobes is defined. That is, since the zero intervals $z_1$, $z_2$, and $z_3$, . . . each define an arbitrary number of zero, a temporal interval between respective vertices of each two main lobes is defined.

Here, description is given on convolution of the first coded ultrasound data 500, the first incompletely-decoded data 501, and the first incompletely-decoded ultrasound echo data 502 with by the filters A and B.

When the first coded ultrasound data 500 is represented as $CD_1$ and the first incompletely-decoded data 501 is represented as $DD_1$, convolution by the filter A is expressed by Math. 10 shown below. In Math. 10, a sign * represents convolution, and Math. 10 expresses convolution of the coded data $CD_1$ with the filter coefficient sequence FA.

$$DD_1=CD_1*FA \quad \text{[Math. 10]}$$

A reception delay profile signal $RxD_i(d)$ for delay-and-sum is expressed by Math. 11 shown below.

$$RxD_i(d) = \frac{\sqrt{d^2 + (p \cdot i)^2} - d}{v} \quad \text{[Math. 11]}$$

In Math. 11, d represents a depth position of the first incompletely-decoded ultrasound echo data 502.

Then, addition is performed for each depth position of the first incompletely-decoded ultrasound echo data 502 on the basis of the reception opening center, in accordance with the reception delay profile signal indicating a relative depth relationship.

The filter B for convolving the first coded ultrasound data 500 is expressed by Math. 12 shown below.

$$FB=[fb_1,Z_1,fb_2,Z_2, \ldots ,fb_{n-1},Z_{n-1},fb_n] \quad \text{[Math. 12]}$$

In Math. 12, $fb_i$ represents a filter factor. Math. 12 is also shown in the figure. In the figure, reference signs cr5, cr6, cr7, and cr8 respectively represent a relationship between $fb_1$ in Math. 7 and $S2_1$ in Math. 1, a relationship between $fb_2$ in Math. 7 and $S2_2$ in Math. 1, a relationship between $fb_{n-1}$ in Math. 7 and $S2_{L-1}$ in Math. 1, and a relationship between $fb_n$ in Math. 7 and $S2_L$ in Math. 1.

When convolution data convolved by the filter B is represented as $DD_2$, convolution by the filter B is expressed by Math. 13 shown below.

$$DD_2=CD_2*FB \quad \text{[Math. 13]}$$

In Math. 13, $CD_2$ represents coded reflected ultrasound data, and a sign * represents convolution. Math. 13 expresses convolution of the coded data $CD_2$ with a filter coefficient sequence FB expressed by Math. 12.

When ultrasound echo data is represented as DD, addition by the addition unit 201c is expressed by Math. 14 shown below.

$$DD=DD'_1+DD'_2 \quad \text{[Math. 14]}$$

In Math. 14, $DD'_1$ represents first incompletely-decoded ultrasound echo data, and $DD'_2$ represents second incompletely-decoded ultrasound echo data. This completes the description of the preceding decoders 200, the reception beam former 131, and the succeeding decoder 201. The following describes in detail the internal structure of the preceding decoders 200.

Figure 8:
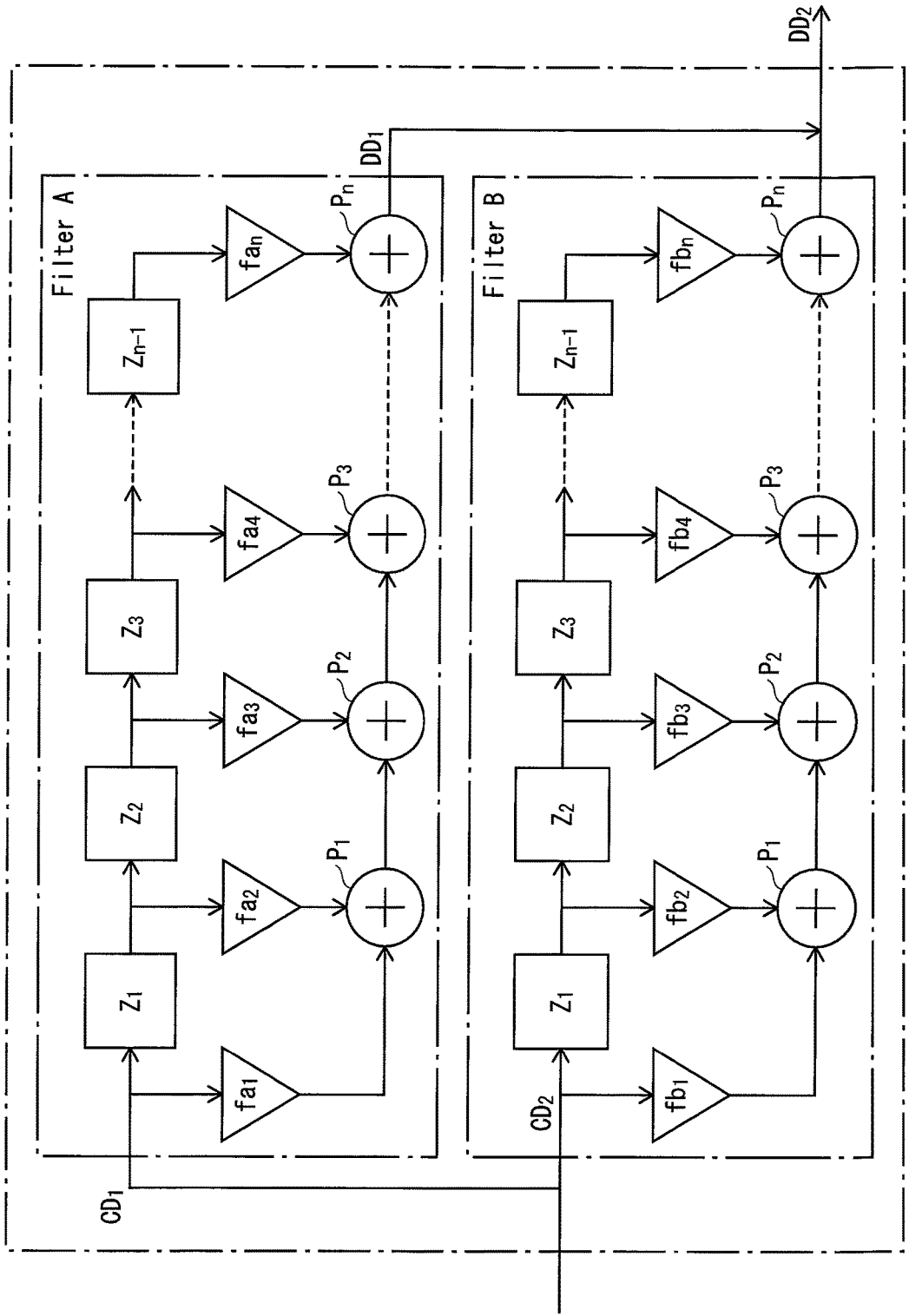
FIG. 8 shows an internal structure of filters A and B.

FIG. 8 shows the internal structure of the filters A and B. The filter A includes n−1 delay circuits (reference signs $Z_1$, $Z_2$, $Z_3$, . . . , $Z_{n-1}$ in the figure), n adder circuits (reference signs $fa_1$, $fa_2$, $fa_3$, . . . , $fa_n$ in the figure), and n multiplier circuits (reference signs $P_1$, $P_2$, $P_3$, . . . , $P_n$ in the figure). The filter A receives an input of first coded data $CD_1$, and outputs first incompletely-decoded data $DD_1$.

The filter B includes n−1 delay circuits (reference signs $Z_1$, $Z_2$, $Z_3$, . . . , $Z_{n-1}$ in the figure), n adder circuits (reference signs $fa_1$, $fa_2$, $fa_3$, . . . , $fa_n$ in the figure), and n multiplier circuits (reference signs $P_1, P_2, P_3, \ldots, P_n$ in the figure). The filter B receives an input of second coded data $CD_2$, and outputs second incompletely-decoded data $DD_2$.

In each of the filters A and B, an arbitrary m-th delay circuit among the n−1 delay circuits is hereinafter referred to as a delay circuit $Z_m$, an arbitrary m-th multiplier circuit among the n multiplier circuits is hereinafter referred to as a multiplier circuit $fa_m$, and an arbitrary m-th adder circuit among the n adder circuits is hereinafter referred to as an adder circuit $P_m$. The delay circuit $Z_m$, the multiplier circuit $fa_m$, and the adder circuit $P_m$ have the common structures with the n−1 delay circuits, the n multiplier circuits, and the n adder circuits, respectively. The following describes the delay circuit $Z_m$, the multiplier circuit $fa_m$, and the adder circuit $P_m$.

The delay circuit $Z_m$ (where m is an arbitrary integer of 1 to n−1) receives an input of first coded data $CD_1$ which has been delayed by the delay circuits $Z_1$ to $Z_{m-1}$, and temporally delays the first coded data $CD_1$ by $Z_m$. The delay circuit $Z_{m-1}$ temporally delays the first coded data $CD_1$ by $Z_1$ because no delay circuit is provided in an input stage of the delay circuit $Z_1$. The delay circuit $Z_2$ temporally delays the first coded data $CD_1$, which has been temporally delayed by $Z_1$, by $Z_2$ because the delay circuit $Z_1$ is provided in an input stage of the delay circuit $Z_2$. The delay circuit $Z_3$ temporally delays the first coded data $CD_1$, which has been temporally delayed by $Z_1$ and $Z_2$, by $Z_3$ because the delay circuits $Z_1$ and $Z_2$ are provided in an input stage of the delay circuit $Z_3$.

The multiplier circuit $fa_m$ (where m is an arbitrary integer of 1 to n−1) receives an input of the first coded data $CD_1$, which has been delayed by the delay circuits $Z_1$ to $Z_{m-1}$, and multiplies the first coded data $CD_1$ by $fa_m$. The multiplier circuit $fa_1$ multiplies the first coded data $CD_1$ by $fa_1$ because no delay circuit is provided in an input stage of the multiplier circuit $fa_1$. The multiplier circuit $fa_2$ multiplies the first coded data $CD_1$, which has been temporally delayed by $Z_1$, by $fa_2$ because the delay circuit $Z_1$ is provided in an input stage of the multiplier circuit $fa_2$. The multiplier circuit $fa_3$ multiplies the first coded data $CD_1$, which has been temporally delayed by $Z_1$ and $Z_2$, by $fa_3$ because the delay circuits $Z_1$ and $Z_2$ are provided in an input stage of the multiplier circuit $fa_3$.

The adder circuit $P_m$ adds an output of the multiplier circuit $fa_{m+1}$, which has been temporally delayed by $Z_1$ to $Z_m$, and an output of the adder circuit $P_{m-1}$, which is the summation of addition results of the adder circuits $P_m$ to $P_{m-2}$. The adder circuit $P_1$ adds the first coded data $CD_1$ and the output of the multiplier circuit $fa_2$, which has been temporally delayed by $Z_1$ because no adder circuit is provided in an input stage of the adder circuit $P_1$. The adder circuit $P_2$ adds the output of the adder circuit $P_1$ and the output of the multiplier circuit $fa_3$, which has been temporally delayed by $Z_1$ and $Z_2$. The adder circuit $P_3$ adds the output of the adder circuit $P_2$ and the output of the multiplier circuit $fa_4$, which has been temporally delayed by $Z_1$, $Z_2$, and $Z_3$. With the circuit configuration described above, the operations in Math. 10 and Math. 13 are performed by the filters A and B that are FIR (finite impulse response) filters.

Figure 9A:
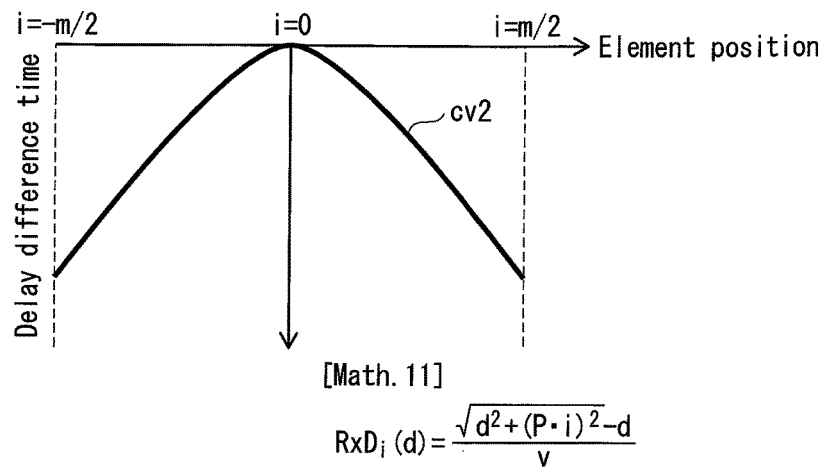
FIG. 9A to FIG. 9C each show a graph representing temporal delay $RxD_i(d)$.

The following describes the reception delay profile signal. FIG. 9A shows a graph cv2 representing the temporal delay $RxD_i(d)$ of the reception delay profile signal. In the graph, the horizontal axis represents a range of the variable i, and the vertical axis represents delay difference time of the temporal delay $RxD_i(d)$. The variable i designates each of the transducer elements 110 included in the ultrasound probe 102, and has a value of −m/2 to m/2. Since the variable i varies within the range of −m/2 to m/2, the term (p·i) in Math. 11 corresponding to the transducer element 110 at the center in the transducer element array has a value of zero. The term (p·i) has a value changing in accordance with the distance from the transducer element 110 at the center in the transducer element array. When i=0 is satisfied, the term (p·i) has a value of zero, and accordingly the numerator in Math. 11 is zero. The more distant from the center the transducer element is, the smaller the numerator in Math. 11 is. A curve cv2 in FIG. 9A represents how the numerator in Math. 11 decreases. The curve cv2 represents temporal change of the temporal delay, with the horizontal axis representing the variable i and the vertical axis representing the delay difference time $RxD_i(d)$.

Figure 9B:
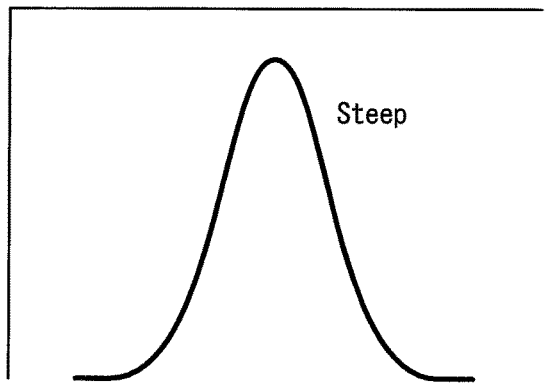
Figure 9C:
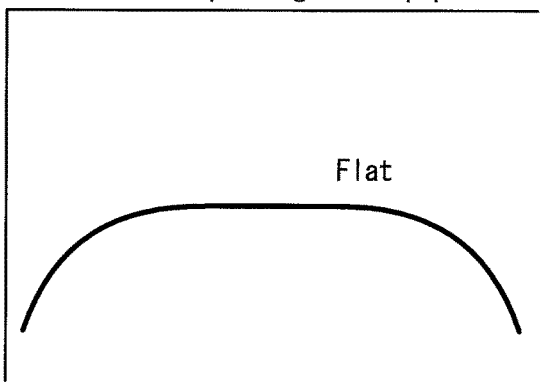

FIG. 9B and FIG. 9C show other variations of the reception beam data. FIG. 9B shows a waveform of the reception beam data with respect to a reflected ultrasound wave reflected off a shallow reflection point. In the case where the reflection point is shallow, the reflected ultrasound wave changes steeply as shown in FIG. 9B. FIG. 9C shows a waveform of the reception beam data with respect to a reflected ultrasound wave reflected off a deep reflection point. In the case where the reflection part is deep, the reflected ultrasound wave changes flatly as shown in FIG. 9C.

The following describes signal storage by the memory 201a and signal addition by the addition unit 201b with reference to FIG. 10 and FIG. 11, respectively.

FIG. 10 shows a process of signal storage by the memory 201a in the transmission event 1. First coded ultrasound data pieces $500i_1$, $500i_2$, $500i_3$, ... each represent a waveform that is obtained by AD conversion, and are each composed of two pulses. First incompletely-decoded data pieces $501i_1$, $501i_2$, $502i_3$, ... each represent a convolution waveform that is obtained by convolution with an impulse response signal performed by a corresponding one of the preceding decoders $200i_1$, $200i_2$, $200i_3$, .... The first incompletely-decoded ultrasound echo data 502 is generated from the first code ultrasound data pieces $500i_1$, $500i_2$, $500i_3$, ..., and represents a waveform that is stored in the memory 201a included in the succeeding decoder 201.

FIG. 11 shows a process of signal addition by the addition unit 201b in the transmission event 2. Second coded ultrasound data pieces $510i_1$, $510i_2$, $510i_3$, ... are each a coded pulse sequence that is obtained by AD conversion performed by a corresponding one of the AD converters $130i_1$, $130i_2$, $130i_3$, .... The second coded ultrasound data pieces $510i_i$, $510i_2$, $510i_3$, ... respectively differ in pulse and code from the first coded ultrasound data pieces $500i_1$, $500i_2$, $500i_3$, .... Second incompletely-decoded data pieces $511i_1$, $511i_2$, $511i_3$, ... are respectively obtained by convolving the second coded ultrasound data pieces $510i_1$, $510i_2$, $510i_3$, ... with an impulse response signal. The time side lobes of the second incompletely-decoded data pieces $511i_1$, $511i_2$, $511i_3$, ... are respectively reversed in phase to the time side lobes of the first incompletely-decoded data pieces $501i_1$, $501i_2$, $501i_3$, .... Second incompletely-decoded ultrasound echo data 512 represents a reception beam waveform that is obtained by delay-and-sum of the second incompletely-decoded data pieces $511i_1$, $511i_2$, $511i_3$, .... The second incompletely-decoded ultrasound echo data 512 has a main lobe having a high wave height. Ultrasound echo data 520 is obtained by adding the first incompletely-decoded ultrasound echo data 502, which is stored in the succeeding decoder 201, and the second incompletely-decoded ultrasound echo data 512. The time side lobes of the first incompletely-decoded ultrasound echo data 502 are reversed in phase to the time side lobes of the second incompletely-decoded ultrasound echo data 512. Accordingly, the addition performed by the succeeding decoder 201 cancels the time side lobes. As a result, the waveform only with the main lobe is obtained.

The ultrasound echo data 520 shown in FIG. 11 is composed of a main lobe 520a. The main lobe 520a has reception ultrasound intensity and depth information from a target inside a subject. Here, an amplitude of the main lobe 520a is amplified by the succeeding decoder 201, and accordingly is higher than an amplitude of a main lobe 502a of the first incompletely-decoded ultrasound echo data 502.

The following describes the relationship among the first incompletely-decoded data 501, the first incompletely-decoded ultrasound echo data 502, the second incompletely-decoded data 511, and the second incompletely-decoded ultrasound echo data 512. FIG. 12A shows the first incompletely-decoded data 501, and FIG. 12B shows the first incompletely-decoded ultrasound echo data 502. FIG. 12C shows the second incompletely-decoded data 511, and FIG. 12D shows the second incompletely-decoded ultrasound echo data 512.

The amplitude of the main lobe 502a of the first incompletely-decoded ultrasound echo data 502 is amplified by the reception beam former 131, and accordingly is higher than an amplitude of a main lobe 501a of the first incompletely-decoded data 501. Similarly, amplitudes of time side lobes 502b of the first incompletely-decoded ultrasound echo data 502 are higher than amplitudes of time side lobes 501b of the first incompletely-decoded data 501.

An amplitude of a main lobe 512a of the second incompletely-decoded ultrasound echo data 512 is amplified by the reception beam former 131, and accordingly is higher than an amplitude of a main lobe 511a of the second incompletely-decoded data 511. Similarly, amplitudes of time side lobes 512b of the second incompletely-decoded ultrasound echo data 512 are higher than amplitudes of time side lobes 511b of the second incompletely-decoded data 511.

When the respective amplitude intensities of the main lobe 501a, the time side lobes 501b, the main lobe 511a, and the time side lobes 511b are represented as $AM_1$, $AS_1$, $AM_2$, and $AS_2$, respectively, conditions in Math. 15 shown below is satisfied.

$$AM_1 > AS_1,\ AM_2 > AS_2 \qquad [\text{Math. 15}]$$

When the respective amplitude intensities of the main lobe 502a, the time side lobes 502b, the main lobe 512a, and the time side lobes 512b are represented as $AM'_1$, $AS'_1$, $AM'_2$, and $AS'_2$, respectively, conditions in Math. 16 shown below is satisfied.

$$AM'_1 > AS'_1,\ AM'_2 > AS'_2 \qquad [\text{Math. 16}]$$

In Math. 16, the inequality $AM'_1 > AS'_1$ expresses that the amplitude of the main lobe 502a is higher than the amplitudes of the time side lobes 502b in FIG. 12B, and the inequality $AM'_2 > AS'_2$ expresses that the amplitude of the main lobe 512a is higher than the amplitudes of the time side lobes 512b in FIG. 12D.

Furthermore, there occurs an error due to delay-and-sum performed by the reception beam former 131 between the time side lobes 502b and the time side lobes 512b. This error due to delay-and-sum between the time side lobes increases as the temporal difference (distance) from the main lobe increases. As a result, a ratio of the main lobe to the time side lobes satisfies a condition in Math. 17 shown below.

$$\frac{AM'_1}{AS'_1} > \frac{AM_1}{AS_1} \qquad [\text{Math. 17}]$$

Math. 17 expresses that the ratio of the amplitude of the main lobe 502a to the amplitudes of the time side lobes 502b in FIG. 12B is larger than the ratio of the amplitude of the main lobe 501a to the amplitudes of the time side lobes 501b in FIG. 12A.

The technical significance of Math. 17 is as described below.

When the number of code words constituting the code sequence increases, the number of the time side lobes 501b and the number of the time side lobes 502b increase, and as a result respective amplitudes of the time side lobes also increase. Specifically, the more distant from the main lobe the time side lobe is, the lower amplitude the time side lobe has. This applies to both the time side lobes 501b and 502b. That is, the more distant from the respective main lobes 501a and 502a the time side lobes 501b and 502b are, the lower amplitudes the time side lobes 501b and 502b similarly have, though the time side lobes 501b and 502b differ from each other in amplitude value. Accordingly, addition processing results in Cancellation of the time side lobes 501b and 502b. Therefore, in the case where a code sequence is long, it is possible to precisely cancel time side lobes.

Figure 13:
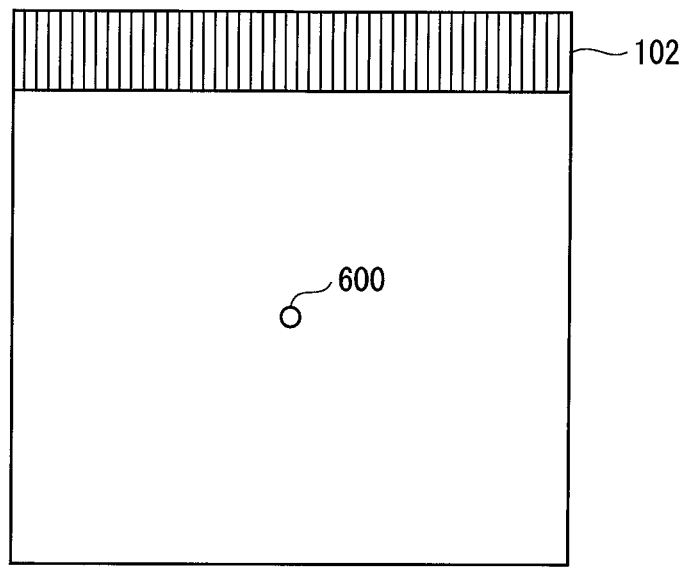
FIG. 13 shows a simulation model relating to ultrasound image generation.

As described above, the ultrasound signal processing device 101 performs decoding processing by dividing a decoding unit to the preceding decoder 200 and the succeeding decoder 201, and thereby reduces a storage region of the decoding unit with no reduction in amplitude of the main lobe and no occurrence of time side lobes. The following describes the effects of the present invention by simulations with reference to FIG. 13 and FIG. 14. FIG. 13 shows a simulation model relating to ultrasound image generation. This simulation model is based on the assumption that the ultrasound probe 102 and a first target 600 are located close to each other in a given space. The transducer elements 110 each transmit a transmission ultrasound signal to the first target 600. The transducer element 110 receives a reflected ultrasound signal that is generated from the transmission ultrasound signal reflected off the first target 600.

Figure 14:
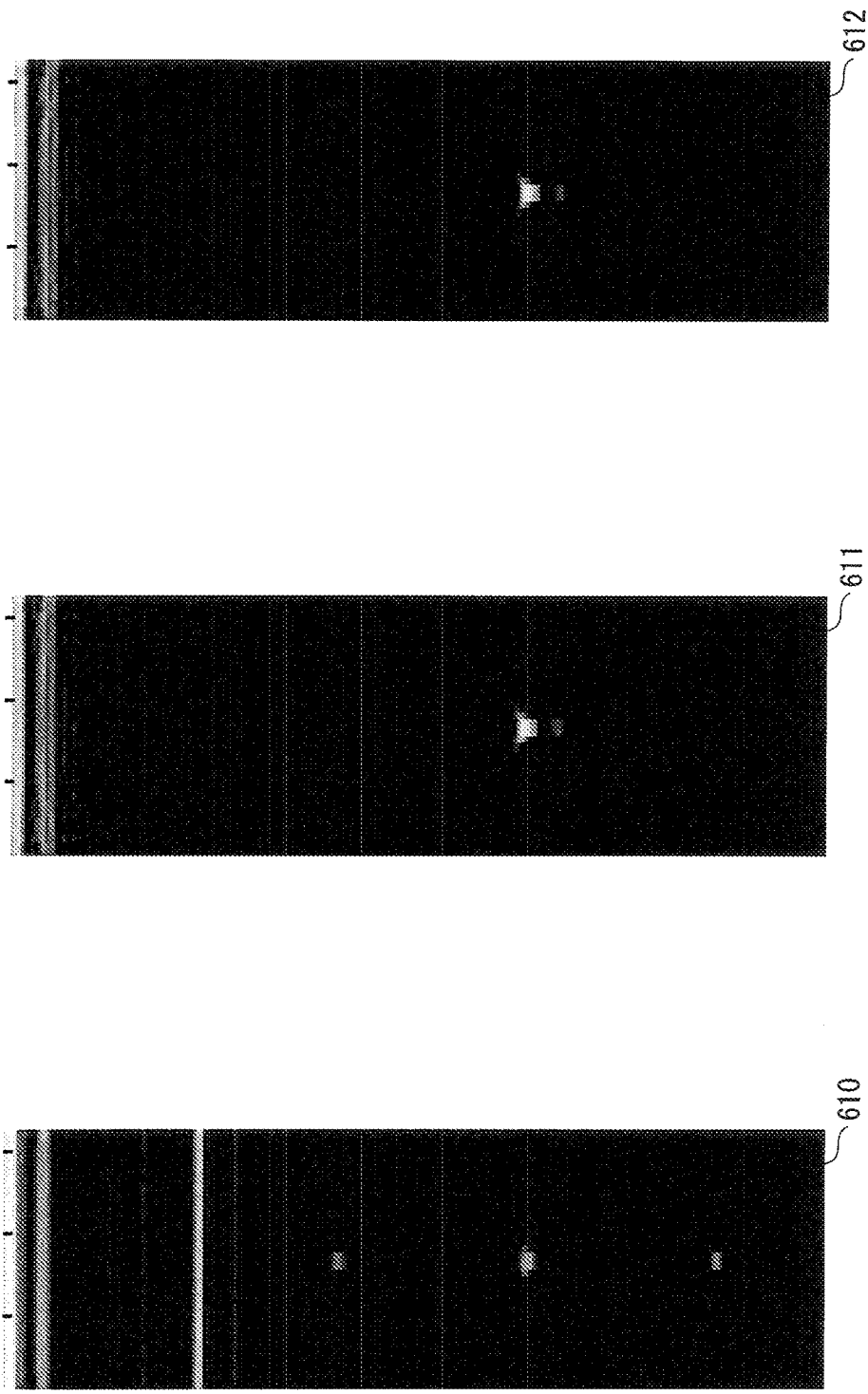
FIG. 14 is an image diagram showing plot of an amplitude intensity of ultrasound echo data 520 generated by performing signal processing on a reception ultrasound signal.

FIG. 14 is an image diagram showing plot of the amplitude intensity of the ultrasound echo data 520 that is generated by performing signal processing on a reception ultrasound signal. Here, respective signal intensities in a DAS decoding method, an RF decoding method, and a proposed decoding method are represented as a DAS decoding method 610, an RF decoding method 611, and proposed decoding method 612, respectively. The DAS decoding method 610 is more influenced by code deterioration due to the reception beam former 131 than the RF decoding method 611 is. Accordingly, the amplitude intensity of the ultrasound echo data 520 decreases at the location of the first target 600. Furthermore, an artifact occurs due to incomplete cancellation of the time side lobes.

The following describes reasons why the amplitude intensity of the ultrasound echo data 520 decreases. According to the DAS decoding method 610, delay-and-sum is performed on reception signals in coded form, and as a result the code shape of the reception signals is lost, and there occurs a notable decrease in amplitude of the main lobe and a notable occurrence of the time side lobes. This results in decrease in amplitude intensity of the ultrasound echo data 520 at the location of the first target 600.

The following describes reasons why the time side lobes of the ultrasound echo data 520 cannot be completely cancelled. The depth position d in Math. 11 of the reception delay profile is casually related to incomplete cancellation of the time side lobes. According to Math. 11 of the reception delay profile, when the depth position d represents a certain amount of distance from the transducer element 110, the shape of the reception delay profile forms a gradual parabolic curve and has little change. Compared with this, when the depth position d represents a short amount of distance from the transducer element 110, the shape of the reception delay profile forms a steep parabolic curve. Accordingly, only a little change of the depth position d causes a great change of the shape of the reception delay profile.

When the distance from the ultrasound probe 102 is short, the reception delay profile steeply changes. Therefore, according to the DAS decoding method 610 in which delay-and-sum is performed on ultrasound data which is in coded form, a code word that is closer to the end of a code sequence has a larger error due to delay-and-sum.

According to the proposed decoding method 612 compared with the RF decoding method 611, the amplitude intensity of the ultrasound echo data 520 does not decrease at the location of the first target 600. This allows the proposed decoding method to reduce the storage region of the succeeding decoder 201 while securing the quality of ultrasound echo data that is equivalent to that in the RF decoding method 611.

The proposed decoding method 612 differs from the RF decoding method 611 in terms of the following point. According to the proposed decoding method 612, delay-and-sum is performed in accordance with the reception delay profile after convolution with an impulse response signal, without an event correlation operation (addition by the succeeding decoder 201). The proposed decoding method 612 is equivalent in quality to the RF decoding method 611 as described above. This is because the quality in the proposed decoding method 612 is influenced by neither an event correlation operation before the delay-and-sum in accordance with the reception delay profile nor an event correlation operation after the delay-and-sum in accordance with the reception delay profile.

This completes the description of the constituent elements of the ultrasound signal processing device 101. The processing by the constituent elements described above is realized as a series of procedures for hardware resources of a computer. The following describes a processing procedure for causing the computer included in the ultrasound signal processing device 101 in order to realize the ultrasound signal processing device 101, with reference to FIG. 15 to FIG. 17.

Figure 15:
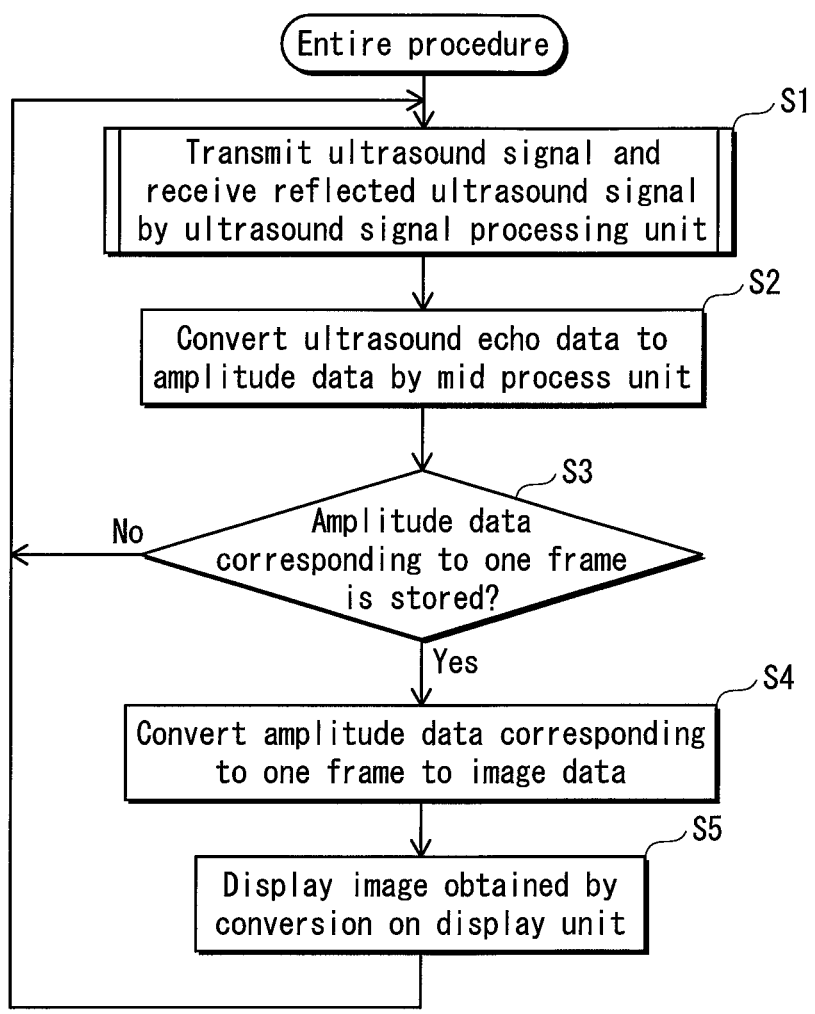
FIG. 15 is a flow chart showing the entire procedure of the ultrasound signal processing device 101.

FIG. 15 is a flow chart showing the entire procedure of the ultrasound signal processing device 101. In this flow chart, a loop structure is defined in which Steps S1 to S5 are repeated. Specifically, the following processing is repeatedly performed. The ultrasound signal processing unit 112 transmits an ultrasound signal, and receives a reflected ultrasound signal to obtain ultrasound echo data (Step S1). The mid process unit 113 converts the ultrasound echo data to amplitude data (Step S2). It is judged as to whether amplitude data pieces corresponding to one frame are stored (Step S3). When the amplitude data pieces corresponding to one frame are stored, the back end process unit 114 converts the amplitude data pieces corresponding to one frame to B-mode image data (Step S4), and the display unit 103 displays an image obtained by the conversion (Step S5). Then, the flow returns to Step S1.

FIG. 16 is a flow chart showing a procedure of ultrasound signal transmission processing. In this flow chart, the following processing is repeatedly performed. A variable i is initialized (Step S11), and a loop of Steps S12 to S20 is executed. Then, a judgment is made as to whether the variable i reaches a value of 198 (Step S21). When the variable i has not yet been reached the value of 198, the variable i is incremented (Step S22), and the flow returns to Step S12.

The processing in Steps S12 to S20 is specifically described below. The processing in Steps S12 to S14 is selectively performed. A variable j for designating an event is initialized by a value of 1 (Step S12). A judgment is made as to whether the variable j is the value of 1 (Step S13). When the variable j is the value of 1, a code sequence $S_1$ is generated (Step S14). Then, the processing in Steps S16 to S18 is successively performed. A transmission delay profile signal is generated by the delay profile generator 121 (Step S16). A code sequence is converted to a transmission beam profile signal with use of the transmission delay profile signal (Step S17). The transducer element transmits a transmission beam profile signal corresponding to an event j (Step S18). Then, a judgment is made as to whether the variable j is a value of 2 (Step S19). When the variable j is the value of 2, the variable j is incremented (Step S20). Then, the flow returns to Step S13.

After the variable j is incremented, the variable j is judged not to be a value of one (Step S13), and a code sequence $S_2$ is generated (Step S15). Then the processing in Steps S16 to S18 is successively performed. A transmission delay profile signal is generated by the delay profile generator 121 (Step S16). The code sequence is converted to a transmission beam profile signal with use of the transmission delay profile signal (Step S17). The transducer element transmits a transmission beam profile signal corresponding to an event j (Step S18). Then, a judgment is made as to whether the variable j is a value of 2 (Step S19). When the variable j is the value of 2 a judgment is made as to whether the variable i reaches the value of 198 (Step S21). When the variable i has not yet been reached the value of 198, the variable i is incremented (Step S22), and the flow returns to Step S12. The processing in Steps S12 to S22 is repeatedly performed until the variable i reaches the value of 198.

FIG. 17 is a flow chart showing a procedure of ultrasound signal reception processing. In this flow chart, the variable i is initialized by a value of 1 (Step S31), and the variable j is initialized by a value of 1 (Step S32). Then, a waiting time is given to wait for receiving a reflected ultrasound signal (Step S33). When the reflected ultrasound signal is received, a judgment is made as to whether the variable j is the value of 1 (Step S34). When the variable j is the value of 1, m transducer element signals $CD_1$ are each convolved with an impulse response waveform of the filter coefficient sequence FA, and thereby m convolution signals $DD_1$ are obtained (Step S35). First incompletely-decoded ultrasound echo data $DD'_1$ is generated from the m convolution signals $DD_1$ (Step S36). Then, the first incompletely-decoded ultrasound echo data $DD'_1$ is written into the memory 201a included in the succeeding decoder 201 (Step S37). The variable j is incremented (Step S38), and then the flow returns to Step S34.

When the variable j is the value of two, the flow proceeds from Step S34 to Step S39, and then m transducer element signals $CD_2$ are each convolved with an impulse response signal, and thereby m convolution signals $DD_2$ are obtained (Step S39). Second incompletely-decoded ultrasound echo data DD'$_2$ corresponding to the event j is generated from the m convolution signals DD$_2$ (Step S40). Then, the first incompletely-decoded ultrasound echo data DD'$_1$ is read from the memory 201a included in the succeeding decoder 201, and the first incompletely-decoded ultrasound echo data DD'$_1$ is added to the second incompletely-decoded ultrasound echo data DD'$_2$ (Step S41). Ultrasound echo data resulting from the addition DD is written, as ultrasound echo data i corresponding to a line i, into a memory included in the mid process unit 113 (Step S42). Then, a judgment is made as to whether the variable i is the value of 198 (Step S43).

When the variable i has not yet been reached the value of 198, the variable i is incremented (Step S44). When the variable i reaches the value of 198, 198 ultrasound echo data pieces are output to the mid process unit 113 (Step S48).

According to the present embodiment as described above, filter processing, that is, convolution with an impulse response waveform is performed on each of RF signals of a plurality of channels that are output from the m transducer elements. Therefore, composition of the RF signals is performed by the reception beam former after noise corresponding to time side lobes of the RF signals is attenuated. Since the noise corresponding to the time side lobes is attenuated before composition by the reception beam former, the quality of ultrasound images is not 20F lower than that in the case where filter processing is performed in a succeeding stage of the reception beam former.

Reception beam data pieces that are output from the reception beam former in respective transmission events are stored in the memory. When a new reception beam data piece is output from the reception beam former in a new transmission event, the new reception beam data piece is added to a reception beam data piece, which has been output immediately before the new reception beam data piece and is stored in the memory. Therefore, the memory only needs to have a size for storing the last one reception beam data piece. Therefore, a necessary size of the memory is smaller than that in the case where the decoder is provided in a preceding stage of the reception beam former.

<Remarks>

Although the above description has been provided on the most preferred embodiment known to the applicant at the time of filing the application, further improvement and modification may be performed on the following technical topics.

(Application to Nondestructive Inspection Device)

FIG. 1 shows the embodiment of the ultrasound signal processing device on the assumption that the ultrasound signal processing device is used in an ultrasound diagnostic system. However, this is just an example. The ultrasound signal processing device may be used in a nondestructive inspection system for inspecting the inside of machines and buildings by ultrasound. Alternatively, the ultrasound signal processing device may be used in an internal inspection system in nuclear facilities, a submarine explosion system, and so on.

(Number of Phase of Golay Code).

The binary phase codes have been used above as the Golay codes. Alternatively, multi-phase codes of three or more phases may be used.

(Aspect of Correlation Operation by Succeeding Decoder)

The correlation operation by the succeeding decoder is an add operation of ultrasound echo data corresponding to a past transmission event, which is stored in the memory, and new ultrasound echo data. However, this is just an example in the case where operation targets are binary phase Golay codes. The correlation operation by the succeeding decoder may include any operations performed by a so-called correlator. Specifically, ultrasound echo data to be stored in the memory may be ultrasound echo data corresponding to an arbitrary past event, and the add operation of ultrasound echo data may be a product-sum operation or a vector operation. In the add operation, weighting may be performed, and the weighting may be performed with a varying weight value.

(Number of Preceding Decoders)

The number of the preceding decoders has been described as equal to the number of the RF signals of the plurality of channels corresponding to the number of the transducer elements. Alternatively, the number of the preceding decoders may be less than the number of the transducer elements. This is because there is a case where the quality is not influenced so much even if. RF signals output from part of the transducer elements are excluded from targets of filter processing. On the contrary, the number of the preceding decoders may be greater than the number of the transducer element signals corresponding to the number of the transducer elements. This is because a large number of preceding decoders can be set in the case where a large scale integrated circuit is used.

(Number of Succeeding Decoders)

The number of the succeeding decoders has been described as one. Alternatively, the number of the succeeding decoders 201 only needs to be less than the number of the preceding decoders. Further alternatively, a plurality of succeeding decoders that are connected in parallel with each other may be alternatively used.

(Implementation in Ultrasound Probe)

In FIG. 2, the ultrasound signal processing unit 112 includes the encoder 120, the delay profile generator 121, the transmission beam former 122, the element driving unit 123, the AD converters 130, the reception beam former 131, the preceding decoders 200, and the succeeding decoder 201. Alternatively, part of these constituent elements may be implemented in the ultrasound probe 102.

(Configuration of Code Sequence Signal)

A Golay code constituting a code sequence signal may be formed from a Golay code pattern that has been stored beforehand in a memory or the like may be used. Alternatively, a Golay code pattern that is set by an operator may be used.

(Implementation in Computer System)

In the case where all or part of each of the above devices is constituted from a computer system including a microprocessor, a ROM, a RAM, a hard disk unit, and so on, the RAM or the hard disk unit should desirably store therein a computer program achieving the operations that are the same as those of the above devices. The functions of each of the devices are achieved by the microprocessor operating in accordance with the computer program.

(Circuit Integration)

Part or all of the constituent elements of each of the above devices may be constituted from a system LSI (Large Scale Integration). A system LSI is an ultra-multifunctional LSI produced by integrating multiple components on one chip, and more specifically, is a computer system including a microprocessor, a ROM, a RAM, and so on. The RAM stores therein a computer program achieving the operations that are the same as those of the above devices. The functions of the LSI are achieved by the microprocessor operating in accordance with the computer program. Furthermore, the method of circuit integration is not limited to LSIs, and implementation through a dedicated circuit or a general-purpose processor is also possible. A field programmable gate array (FPGA) that allows programming after LSI manufacturing or a reconfigurable processor that allows reconfiguration of connections and settings of circuit cells inside the LSI may also be used.

(Modularization)

Part or all of the constituent elements of each of the above devices may be constituted from an IC card detachable from each of the devices or as a single module. The IC card or the module is constituted from a computer system including a microprocessor, a ROM, a RAM, and so on. The IC card or the module may include the above ultra-multifunctional LSI. The functions of the IC card or the module are achieved by the microprocessor operating in accordance with the computer program. The IC card or the module may be tamper resistant.

(Programming)

The present invention may be methods that are realized through the above processing by the computer. Alternatively, the present invention may be a computer program that is realized by a processor such as a CPU executing the methods or a digital signal constituted from the computer program.

Alternatively, the present invention may be a computer-readable recording medium in which the computer program or the digital signal is recorded. The computer-readable recording medium is for example a flexible disk, a hard disk, a CD-ROM, an MO, a DVD, a DVD-ROM, a DVD-RAM, a BD (Blu-ray Disc), or a semiconductor memory. Alternatively, the present invention may be the digital signal recorded in the computer-readable recording medium. Alternatively, the present invention may be the computer program or the digital signal to be transmitted via networks, of which electric communication networks, wire or wireless communications networks, and the Internet are representative, via data broadcasting, or the like.

Alternatively, the present invention may be a computer system including a microprocessor and a memory. The memory may store therein the computer program, and the microprocessor may operate in accordance with the computer program.

Alternatively, the present invention may be implemented by another computer system, by transmitting the computer program or the digital signal recorded in the recording medium to the other computer system, or by transmitting the computer program or the digital signal to the other computer system via the networks or the like.

(Combination of Embodiment)

The above embodiment and modifications may be combined with each other.

Also, all the numerical figures used above are given as examples to specifically describe the present invention, and therefore the present invention is not limited by such illustrative numerical figures.

Separation of the functional blocks in the block diagrams is merely an example, and plurality of functional blocks may be implemented as a single functional block, a single functional block may be separated into a plurality of functional blocks, or part of functions of a functional block may be transferred to another functional block. Furthermore, the functions of functional blocks having similar functions may be processed in parallel or in time division by single hardware or software.

The sequence in which the above steps are executed is given as an example to specifically describe the present invention, and therefore other sequences are possible. Furthermore, part of the above steps may be executed simultaneously (in parallel) with another step.

Moreover, the present invention includes various types of modifications obtainable through modifications to the embodiments that may be conceived of by a person skilled in the art, as long as such modifications do not cause deviation from the general concept of the present invention.

Although the present invention has been fully described by way of examples with reference to the accompanying drawings, it is to be noted that various changes and modifications will be apparent to those skilled in the art. Therefore, unless such changes and modifications depart from the scope of the present invention, they should be construed as being included therein.

What is claimed is:

1. An ultrasound signal processing device that outputs a plurality of code sequences to a transducer element array to cause the transducer element array to transmit ultrasound and receive reflected ultrasound, the code sequences each having a different arrangement of a plurality of code words, the ultrasound signal processing device comprising:

M preceding decoders that (i) receive N transducer element reception signals which are generated by the transducer element array from the received reflected ultrasound and output to the M preceding decoders from the transducer element array upon reception of the reflected ultrasound, and (ii) obtain N convolution signals by convolving each of the N transducer element reception signals with an impulse response signal, and (iii) output the N convolution signals, where M is an integer satisfying $2 \leq M \leq N$;

a reception beam former that (i) receives the N convolution signals output from the M preceding decoders, (ii) obtains a plurality of reception beam signals one-to-one corresponding to the code sequences by performing delay-and-sum on each of the N convolution signals output from the M preceding decoders, and (iii) outputs the plurality of reception beam signals; and L succeeding decoders that (i) receive the plurality of reception beam signals output from the reception beam former, and (ii) obtain ultrasound echo data by performing a correlation operation on each of the reception beam signals output from the reception beam former, based on the code words included in the code sequence corresponding to the reception beam signal, where L is an integer satisfying $1 \leq L \leq M$.

2. The ultrasound signal processing device of claim 1, wherein the reception beam signals are each an incompletely-decoded ultrasound echo signal, a main lobe and time side lobes of the incompletely-decoded ultrasound echo signal are respectively higher in wave height than a main lobe and time side lobes of the transducer element signal, and a ratio in wave height of the main lobe to the time side lobes of the incompletely-decoded ultrasound echo signal is higher than a ratio in wave height of a main lobe to time side lobes of the convolution signal.

3. The ultrasound signal processing device of claim 1, wherein the M preceding decoders are equal in number to N transducer elements constituting the transducer element array, and the L succeeding decoders are fewer in number than the M preceding decoders.

4. The ultrasound signal processing device of claim 1, wherein the code sequences include a first code sequence and a second code sequence, and correlation between the code words indicates that a sum of an autocorrelation function of a portion of the code words included in the first code sequence and a portion of the code words included in the second code sequence is zero.

5. The ultrasound signal processing device of claim 4, wherein the preceding decoders each include a plurality of finite impulse response filters, and the finite impulse response filters one-to-one correspond to the code sequences, and differ in filter coefficient value from each other.

6. The ultrasound signal processing device of claim 5, wherein when the reception beam former outputs a first reception beam signal corresponding to the first code sequence, the succeeding decoder stores the first reception beam signal in a memory included therein, and when the reception beam former outputs a second reception beam signal corresponding to the second code sequence, the succeeding decoder performs the delay-and-sum by adding the first reception beam signal stored in the memory and the second reception beam signal to cancel time side lobes of the second reception beam signal.

7. The ultrasound signal processing device of claim 1, further comprising:

an encoder that generates a code sequence for each transmission event;

a delay profile generator that generates a transmission delay profile signal corresponding to each focal point that is generated from the transmitted ultrasound; and a transmission beam former that generates a transmission beam profile signal based on the code sequence and the transmission delay profile signal, the transmission beam profile signal having waveform information of a driving signal for driving one of transducer elements constituting the transducer element array and having drive timing information of the transducer element, wherein the code sequence is output from the transducer element that is driven in accordance with the transmission beam profile signal.

8. An ultrasound signal processing method of outputting a plurality of code sequences to a transducer element array to cause the transducer element array to transmit ultrasound and receive reflected ultrasound, the code sequences each having a different arrangement of a plurality of code words, the ultrasound signal processing method comprising:

M preceding decoding that includes: (i) receiving N transducer element reception signals which are generated by the transducer element array from the received reflected ultrasound and output from the transducer element array upon reception of the reflected ultrasound, and (ii) obtaining N convolution signals by convolving each of the N transducer element reception signals with an impulse response signal, and (iii) outputting the N convolution signals, where M is an integer satisfying $2 \leq M \leq N$;

reception beam forming that includes: (i) receiving the N convolution signals output from the M preceding decoders, (ii) obtaining a plurality of reception beam signals one-to-one corresponding to the code sequences by performing delay-and-sum on each of the N convolution signals output from the M preceding decoding, and (iii) outputting the plurality of reception beam signals; and L succeeding decoding that includes: (i) receiving the plurality of reception beam signals output from the reception beam forming, and (ii) obtaining ultrasound echo data by performing a correlation operation on each of the reception beam signals output from the reception beam forming, based on the code words included in the code sequence corresponding to the reception beam signal, where L is an integer satisfying $1 \leq L \leq M$.

9. A non-transitory computer-readable recording medium having recorded therein a program for causing a computer to execute the ultrasound diagnostic method of claim 8.

* * * * *